US009353058B2

(12) United States Patent
Zeligs

(10) Patent No.: US 9,353,058 B2
(45) Date of Patent: *May 31, 2016

(54) ANTI-PARASITIC METHODS AND COMPOSITIONS UTILIZING DIINDOLYLMETHANE-RELATED INDOLES

(71) Applicant: BioResponse, L.L.C., Boulder, CO (US)

(72) Inventor: Michael A. Zeligs, Boulder, CO (US)

(73) Assignee: BioResponse, L.L.C., Boulder, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/051,248

(22) Filed: Oct. 10, 2013

(65) Prior Publication Data
US 2014/0037577 A1    Feb. 6, 2014

Related U.S. Application Data

(62) Division of application No. 12/447,307, filed as application No. PCT/US2007/022649 on Oct. 26, 2007, now Pat. No. 8,586,621.

(60) Provisional application No. 60/854,830, filed on Oct. 27, 2006.

(51) Int. Cl.
| A61K 31/40 | (2006.01) |
| C07D 209/04 | (2006.01) |
| A61K 31/405 | (2006.01) |
| A61K 45/06 | (2006.01) |
| A61K 31/12 | (2006.01) |
| A61K 31/155 | (2006.01) |
| A61K 31/357 | (2006.01) |
| A61K 31/404 | (2006.01) |
| A61K 31/407 | (2006.01) |
| A61K 31/4164 | (2006.01) |
| A61K 31/4706 | (2006.01) |
| A61K 31/49 | (2006.01) |
| A61K 31/59 | (2006.01) |
| A61K 33/24 | (2006.01) |
| A61K 36/00 | (2006.01) |
| A61K 36/06 | (2006.01) |
| A61K 36/258 | (2006.01) |
| A61K 36/886 | (2006.01) |
| A61K 36/8962 | (2006.01) |
| A61K 38/19 | (2006.01) |
| C07D 209/52 | (2006.01) |

(52) U.S. Cl.
CPC .............. C07D 209/04 (2013.01); A61K 31/12 (2013.01); A61K 31/155 (2013.01); A61K 31/357 (2013.01); A61K 31/404 (2013.01); A61K 31/405 (2013.01); A61K 31/407 (2013.01); A61K 31/4164 (2013.01); A61K 31/4706 (2013.01); A61K 31/49 (2013.01); A61K 31/59 (2013.01); A61K 33/24 (2013.01); A61K 36/00 (2013.01); A61K 36/06 (2013.01); A61K 36/258 (2013.01); A61K 36/886 (2013.01); A61K 36/8962 (2013.01); A61K 38/193 (2013.01); A61K 45/06 (2013.01); C07D 209/52 (2013.01)

(58) Field of Classification Search
CPC ..................................................... A61K 31/404
USPC .......................................................... 514/420
See application file for complete search history.

(56) References Cited

U.S. PATENT DOCUMENTS

| 5,635,215 | A |  | 6/1997 | Boschetti et al. |
| 5,718,921 | A |  | 2/1998 | Mathiowitz et al. |
| 5,830,887 | A |  | 11/1998 | Kelly |
| 5,895,787 | A |  | 4/1999 | Arffmann et al. |
| 5,948,808 | A |  | 9/1999 | Safe |
| 6,086,915 | A |  | 7/2000 | Zeligs et al. |
| 6,399,645 | B1 |  | 6/2002 | Bell et al. |
| 6,477,229 | B1 |  | 11/2002 | Grosser |
| 6,534,085 | B1 | * | 3/2003 | Zeligs ........................... 424/451 |
| 6,583,167 | B2 |  | 6/2003 | Palmer et al. |
| 6,613,792 | B1 |  | 9/2003 | Ellenberger et al. |
| 6,656,963 | B2 |  | 12/2003 | Firestone et al. |
| 6,689,387 | B1 |  | 2/2004 | Zeligs |
| 6,800,655 | B2 |  | 10/2004 | Jong et al. |
| 7,348,352 | B2 |  | 3/2008 | Zeligs |
| 7,384,971 | B2 |  | 6/2008 | Zeligs |

(Continued)

FOREIGN PATENT DOCUMENTS

| EP | 0566226 | 10/1993 |
| WO | WO 96/30347 | 3/1996 |

(Continued)

OTHER PUBLICATIONS

Rumore "Vitamin A as a immunomodulating Agent," Clinical Pharmacy, 1993, vol. 12, No. 7, pp. 506-514, Medline Abstract, AN 1993358590.*

(Continued)

Primary Examiner — Shengjun Wang
(74) Attorney, Agent, or Firm — Jones Day

(57) ABSTRACT

The present invention includes methods and compositions for the treatment and prevention of protozoal parasitic infections utilizing Diindolylmethane-related indoles. Additive and synergistic interaction of Diindolylmethane-related indoles with other known anti-parasitic and pro-apoptotic agents is believed to permit more effective therapy and prevention of protozoal parasitic infections. The methods and compositions described provide new treatment of protozoal parasitic diseases of mammals and birds including malaria, leishmaniasis, trypanosomiasis, trichomoniasis, neosporosis and coccidiosis.

46 Claims, No Drawings

(56) References Cited

U.S. PATENT DOCUMENTS

| | | | |
|---|---|---|---|
| 7,384,972 B2 | 6/2008 | Zeligs | |
| 7,709,520 B2 | 5/2010 | Safe | |
| 7,989,486 B2 | 8/2011 | Zeligs | |
| 8,080,577 B2 | 12/2011 | Zeligs | |
| 8,586,621 B2 | 11/2013 | Zeligs | |
| 2002/0147155 A1 | 10/2002 | Foster et al. | |
| 2003/0211165 A1 | 11/2003 | Vogel et al. | |
| 2003/0220377 A1 | 11/2003 | Chesworth | |
| 2003/0223956 A1 | 12/2003 | Goupil et al. | |
| 2004/0022760 A1 | 2/2004 | McKenna et al. | |
| 2004/0142000 A1 | 7/2004 | Suga et al. | |
| 2005/0158347 A1 | 7/2005 | Tarleton et al. | |
| 2005/0232869 A1* | 10/2005 | Tamarkin et al. | 424/45 |
| 2006/0100264 A1* | 5/2006 | Bjeldanes et al. | 514/414 |
| 2006/0229355 A1 | 10/2006 | Bjeldanes et al. | |
| 2008/0145418 A1 | 6/2008 | Zeligs | |

FOREIGN PATENT DOCUMENTS

| | | | |
|---|---|---|---|
| WO | WO 96/33980 | 10/1996 | |
| WO | WO 97/02266 | 1/1997 | |
| WO | WO 97/30034 | 8/1997 | |
| WO | WO 97/38983 | 10/1997 | |
| WO | WO 99/55683 | 11/1999 | |
| WO | WO 00/02857 | 1/2000 | |
| WO | WO 00/31048 | 6/2000 | |
| WO | WO 01/20990 | 3/2001 | |
| WO | WO 02/092575 | 11/2002 | |
| WO | WO 2004/071425 | 5/2004 | |
| WO | WO 2005/107747 | 11/2005 | |
| WO | WO 2006/047716 | 5/2006 | |
| WO | WO 2006/053160 | 5/2006 | |
| WO | WO 2006053160 | * 5/2006 | |

OTHER PUBLICATIONS

Chebotaryov et al. "Rehabilitative treatment of women with complicated forms of urogenital trichomoniasis," Vestnik Dermatologii i Venerologii, 2002 No. 2, pp. 66-67, Biosis Abstract, AN 2002:361680.*

Aggarwal & Ichikawa, 2005, "Molecular targets and anticancer potential of indole-3-carbinol and its derivatives," Cell Cycle 4(9):1201-15.

Akkar et al., 2003, "Formulation of intravenous carbamazepine emulsions by SolEmuls technology," Eur J. Pharm Biopharm. 55:305-12.

Baugh et al., 1998, Jan. 23, "Treatment of cervical dysplasia with indole-3-carbinol" in The Ray A. Barlow Scientific Symposium, Shreveport : The Center for Excellence in Cancer Research, Treatment and Education, Louisiana State University Medical Center, Shreveport (LA), p. 3.

Bell et al., 1999, Mar., "Placebo-controlled Trial of Indole-3-Carbinol in the Treatment of Cervical Dysplasia", Abstracts Presented for the Thirtieth Annual Meeting of the Society of Gynecologic Oncologists, Gynecol. Oncol. 72: 443-527 (Abstract 13).

Bell et al., 2000, Placebo-Controlled Trial of Indole-3-Carbinol in the Treatment of CIN, Gynecologic Oncology 78:123-129.

Bioresponse Letter, Dec. 29, 1998.

Bioresponse-DIM Indolplex Product Information Brochure, Dec. 15, 1998.

Bjeldanes et al., 1991, "Aromatic hydrocarbon responsiveness-receptor agonists generated from indole-3-carbinol in vitro and in vivo: comparisons with 2,3,7,8,-tetrachlorodibenzo-p-dioxin," Proc. Natl. Acad. Sci. USA 88:9543-9547.

Bonnesen et al., 2001, "Dietary indoles and isothiocyanates that are generated from calciferous vegetables can both induce apoptosis and confer protection against DNA damage in human colon cell lines," Cancer Research, American Association for Cancer Research 61:6120-6130.

Bradfield et al., 1987, "High-performance liquid chromatographic analysis of anticarcinogenic indoles in Brassica oleracea," J Agric Food Chem 35:46-49.

Bradfield et al., 1987, "Structure-Activity relationships of dietary indoles: a proposed mechanism of action as modifiers of xenobiotic metabolism," J Toxicol Environ Health 21:311-23.

Bradlow et al., 1999, "Multifunctional aspects of the action of indole-3-carbinol as an anti-tumor agent," Annals of New York Academy of Sciences 889: 204-213.

Bradlow et al., 1996, "2-hydroxyestrone: the 'good' estrogen," J Endocrin 150:S259-S265.

Brandi et al., 2003, "A new indole-3-carbinol tetrameric derivative inhibits cyclin-dependent kinase 6 expression, and induces G1 cell cycle arrest in both estrogen-dependent and estrogen-independent breast cancer cell lines," Cancer Res. 63(14):4028-36.

Calabro et al, 2005, "Inhibition of Tumor-Necrosis-Factor-α Induced Endothelial Cell Activation by a New Class of PPAR-γ: Agonists An in vitro Study Showing Receptor-Independent Effects," J Vasc Res;42:509-516.

Chang et al., 1999, "Cytostatic and antiestrogenic effects of 2-(Indo1-3-ylmethyl)-3,3'-diindolylmethane, a major in vivo product of dietary indole-3-carbinol," Biochem. Pharmacol. 58:825-834.

Chen et al., 1998, "Aryl hydrocarbon receptor-mediated antiestrogenic and antitumorigenic activity of diindoylmethane," Carcinogenesis 19:1631-1639.

Chen et al., 2001, "Indole-3-carbinol and diindolylmethane induce apoptosis of human cervical cancer cells and in murine HPV16-transgenic preneoplastic cervical epithelium," J Nutr. 131:3294-302.

Dashwood, 1998, "Indole-3-carbinol: anticarcinogen or tumor promoter in brassica vegetables?" Chem Biol. Interact. 110(1-2):1-5.

de Kruif et al., 1991, ". Structure elucidation of acid reaction products of indole-3-carbinol: detection in vivo and enzyme induction in vitro," Chem Biol Interact. 80:803-15.

Del Cacho, 2004, "Expression of anti-apoptotic factors in cells parasitized by second-generation schizonts of *Eimeria tenella* and *Eimeria necatrix*," Vetinary Parasitology 125:287-300.

Del Prete, 1998, "The Concept of Type-1 and Type-2 Helper T Cells and Their Cytokines in Humans," Int Rev Immunol. 16(3-4): 427-55.

Exon et al., 2000, "Dietary indole-3-carbinol alters immune functions in rats," J. Toxicol. Environ. Health A. 59(4):271-9.

Gao et al., 2002, "Endocrine disruption by indole-3-carbinol and tamoxifen: blockage of ovulation," Toxicol Appl Pharmacol. 183:179-88.

Gillner et al., 1985, "Interactions of indoles with specific binding sites for 2,3,7,8-tetrachlorodibenzo-p-dioxin in rat liver," Mol Pharmacol 28:357-363.

Hardman, et al., "Goodman & Gilman's The Pharmacological Basis of Therapeutics" ($9^{th}$ ed, 1996), pp. 51 and 57-58.

Hong et al., 2002, "Bcl-2 family-mediated apoptotic effects of 3,3'-diindolylmethane (DIM) in human breast cancer cells," Biochem Pharmacol. 63:1085-97.

Howard et al., 1989, "Intracerebral drug delivery in rats with lesion-induced memory deficits," J Neurosurg. 71:105-12.

Jin et al., 1999, "Indole-3-carbinol prevents cervical cancer in human papillomavirus type 16 (HPV16) transgenic mice," Cancer Res 59:3991-7.

Langer and Peppas, 1983, "Chemical and physical structure of Polymers as carriers sfor controlled release of bioactive agents: a review," J. Macromol Sci Rec Macromol. Chem. 23:61-126.

Langer et al., 1990, New methods of drug delivery, Science 249:1527-1533.

Larsen-Su et al., 2001, "Transplacental exposure to indole-3-carbinol induces sex-specific expression of CYP1A1 and CYP1B1 in the liver of Fischer 344 neonatal rats," Toxicological Sci. 64:162-168.

Leong et al., 2004, "Potent ligand-independent estrogen receptor activation by 3,3'-diindolylmethane is mediated by cross talk between the protein kinase a and mitogen-activated protein kinase signaling pathways," Mol Endocrinol. 18:291-302.

Liu et al., 1994, "Indolo[3,2-b]carbozole: a dietary-derived factor that exhibits both antiestrogenic and estrogenic activity," J. Natl. Cancer Inst. 86:1758-1765.

Loria et al., 1990, "Immune response facilitation and resistance to virus and bacterial infectionis with dehydroepiandrosterone (DHEA)," Biologic Role of Dehydroepiandrosterone, pp. 107-130.

(56) References Cited

OTHER PUBLICATIONS

Loub et al., 1975, "Aryl hydrocarbon hydroxylase induction in rat tissues by naturally occurring indoles of cruciferous plants," J. Natl. Cancer Inst. 54:985-988.
Michnovicz et al., 1997, "Changes in levels of urinary estrogen metabolites after oral indole-3-carbinol treatment in humans", J. Natl. Cancer Inst. 89:718-23.
Morfin R et al., 1994, "Pregnenolone and dehydroepiandrosterone as precursors of native 7-hydroxylated metabolites which increase the immune response in mice," J of Steroid Biochemistry and Molecular Biology, Elsevier Science Ltd., Oxford, GB, vol. 50(1/2) Jul. 1994, pp. 91-100.
Muzandu et al., 2005, "Lycopene and beta-carotene ameliorate catechol estrogen-mediated DNA damage," Jpn J Vet Res. 52:173-84.
Raiiman et al., 2005, "Inhibition of Nuclear Translocation of Nuclear Factor-kB Breast Cancer Cells Contributes to 3,3'-Diindolylmethane-Induced Apoptosis in," Cancer Res. 65:364-371.
Räth et al., 2004, "Pharmacokinetic study of artemisinin after oral intake of a traditional preparation of *Artemisia annua* L. (annual wormwood)," Am. J .Trop. Med. Hyg. 70(2):128-132.
Riby et al., 2000, "Ligand-independent activation of estrogen receptor function by 3,3'-diindolylmethane in human breast cancer cells," Biochem. Pharmacol. 60:167-177.
Ritter et al., 2001, "Oxidations of 17beta-estradiol and estrone and their interconversions catalyzed by liver, mammary gland and mammary tumor after acute and chronic treatment of rats with indole-3-carbinol or beta-naphthoflavine," Can. J. Physiol. Pharmacol. 79(6):519-32.
Rogan, 2006, "The natural chemopreventive compound indole-3-carbinol: state of the science," In Vivo. 20(2):221-8. Review.
Rosen et al, 1998, "Preliminary results of the use of indolc-3-carbinol for recurrent respiratory papillomatosis," Otolaryngol Head Neck Surg 118:810-5.
Roy et al, 2008,"An insight into the mechanism of inhibition of unusual bi-subunittopoisomerase I from *Leishmania donovani* by 3,3-di-indolylmethane, a novel DNA topoisomerase I poison with a strong binding affinity to the enzyme," Biochem. J. 409:611 622.
Roy et al., 2008, "Mitochondria-Dependent Reactive Oxygen Species-Mediated Programmed Cell Death Induced by 3,3-Diindolylmethane through Inhibition of F0F1-ATP Synthase in Unicellular Protozoan Parasite *Leishmania donovani*," Mol Pharmacol. 74:1292-1307.
Saudek et al., 1989, "A preliminary trial of the programmable implantable medication system for insulin delivery," New Engl. J. Med. 321:574-79.
Sefton, 1987, "Implantable pumps," CRC Crit Ref., Biomed Eng. 14:201.
Sepkovic et al., 2001, "Quantitative Determination of 3,3'-Diindolymethane in the urine of individuals receiving indole-3-carbinol," Nutr Cancer. 41(1-2):57-63.
Shilling et al., 2001, "3,3' -diindolylmethane, a major condensation product of indole-3-carbinol, is a potent estrogen in the rainbow trout," Toxicology and Applied Pharmacology 170:191-200.
Smaill et al., 1999, "Tyrosine kinase inhibitors. 15. 4-(Phenylamino)quinazoline and 4-(phenylamino)pyrido[d]pyrimidine acrylamides as irreversible inhibitors of the ATP binding site of the epidermal growth factor receptor," J Med Chem. 42:1803-1815.
Stewart et al., 2004, "Resveratrol antagonizes EGFR-dependent Erk1/2 activation in human androgen-independent prostate cancer cells with associated isozyme-selective PKC alpha inhibition," Invest. New Drugs 22:107-117.
Stresser et al., 1995, "Mechanisms of tumor modulation by indole-3-carbinol: disposition and excretion in male fisher 344 rats," Drug Metabolism and Disposition 23:965-975.
Stresser et al., 1995, "The anticarcinogen 3,3'-Diindolyl-methane is an inhibitor of cytochrome P-450," J. Biochem. Toxicol. 10(4):191-201.
Tse et al., 1987, "Disposition of alpha-[(dimethylamino)methyl]-2-(3-ethyl-5-methyl-4-isoxazolyl)-1H-indole-3-methanol (59-801), a hypoglycaemic agent in rats, dogs and monkeys," Xenobiotica 17(6):741-9.
Woodburn et al, 1999, "The epidermal growth factor receptor and its inhibition in cancer," Pharmacol. Ther. 82:241-250.
Yuan F et al., Jan. 9-15, 1999, "Prevention of Papillomavirus initiated cancer by the phytochemical Indole-3-Carbinol," Proceedings of the 17th International Papillomavirus Conference, p. 73.
Yuhas et al, 1990, "Inhibition of tumor necrosis factor-induced cell killing by tryptophan and indole." Eur. Cytokine Net. 1: 35 - 40.
Zeligs et al., 2002, "Absorption-enhanced 3,3-dindolylmethane: human use in HPV-related, benign and pre-cancerous conditions," Proceedings of the Annual Meeting of the American Association for Cancer Research, New York, NY vol. 43, Mar. (Mar. 2002), p. 664, Abstract 3198.
Zeligs, 1998, "Diet and Estrogen Status: The Cruciferous Connection," J Med Food 1:67-82.
International Search Report, dated Sep. 22, 2008 of PCT/US2007/022649 now published as WO2008/057253.
Written Opinion, dated Sep. 22, 2008 of PCT/US2007/022649 now published as WO2008/057253.

* cited by examiner

ANTI-PARASITIC METHODS AND COMPOSITIONS UTILIZING DIINDOLYLMETHANE-RELATED INDOLES

This application is a divisional of U.S. Application Ser. No. 12/447,307, which is the National Stage of International Application No. PCT/US2007/022649, filed on Oct. 26, 2007, which claims the benefit of U.S. Provisional Application No. 60/854,830, filed on Oct. 27, 2006, each of which is incorporated herein by reference in its entirety.

1. FIELD OF THE INVENTION

The present invention relates to methods and compositions for the treatment and prevention of parasitic infections, preferably protozoal parasitic infections, utilizing Diindolylmethane-related indoles. Administration of Diindolylmethane-related indoles, alone or in combination with known antiprotozoal agents, provides a method to selectively promote apoptosis of parasite infected host cells and of extracellular protozoal parasites. Direct pro-apoptotic activity and interaction of Diindolylmethane-related indoles with other known anti-parasitic and pro-apoptotic agents is believed to permit more effective chemotherapy and to be complementary to co-administered anti-protozoal vaccines. The methods and compositions of the present invention provide new therapeutic options in treating the major protozoal parasitic diseases of mammals and birds including malaria, leishmaniasis, trypanosomiasis, neosporosis and coccidiosis.

2. BACKGROUND OF THE INVENTION

2.1 Protozoal Related Disease

Protozoal parasites are single-celled organisms which live during some or all stages of their life cycle within organs, tissues and cells of multicellular, metazoan animals. As parasites, they obtain nutrients either from the host organism's food supply or from its cells and tissues. As eukaryotic unicellular organisms, the protozoal parasites are able to live both within animal cells and as free living extra-cellular parasites residing in the blood, lymph tissue or within the intestinal lumen.

As agents of infection, the protozoal parasites are fundamentally different than bacteria and viruses. Unlike bacteria and viruses, protozoa parasites are animals and share similar metabolism, respiration, and nutritional needs with their animal hosts. The similar metabolism of protozoa to mammalian metabolism renders most antibiotics and antiviral agents, selectively active against bacteria and viruses, respectively, ineffective for protozoal infection. Activity of compounds with antibacterial or antiviral activity against protozoal parasites would be atypical and unexpected. The lack of differences between protozoal metabolism and host cellular metabolism requires novel pharmacologic approaches to find therapeutic agents selective for eliminating protozoal organisms living within an animal host. Unlike bacteria and viruses, protozoa may assume different sexual forms and differentiate into a variety of maturational stages in various organs, presenting unique challenges for recognition by the host immune system. As genetically more complex organisms than bacteria and viruses, protozoa differentiate into forms which resist killing by known microbicides active against bacteria and viruses (Weir et al., 2002, Appl Environ Microbiol. 68(5):2576-9). Development of effective antiprotozoal therapeutics and stimulation of host immune responses against protozoal parasites therefore requires approaches different from those utilized in developing antibacterial, antiviral, and general immune potentiating agents.

The primary protozoal parasites causing disease in man include hemoflagellates of the class Trypanosomatidea, causing Leishmaniasis and Trypanosomiasis, and parasites of the phylum Apicomplexa, class *Coccidea*, causing malaria, toxoplasmosis, cryptosporidiosis, and bebesiosis. Species of *Coccidea* can infect humans, domestic animals and livestock, including poultry, lambs, calves, piglets, and rabbits. Protozoal parasitic diseases related to malaria include disease caused by parasites of the species Neospora. Neospora infections occur in dogs, cattle, sheep, goats and horses.

The majority of populations in developing countries are now at high risk of various protozoal infections including malaria, leishmaniasis, and trypanosomiasis. Together these protozoal diseases cause millions of preventable deaths every year. No preventive or therapeutic vaccines are yet available for these parasitic diseases. The market for drugs against such diseases is limited by poverty and the emergence of resistance to existing single agent chemotherapy. As used herein, chemotherapy refers to the use of chemical substances to treat disease. Due to the lack of protective immunity following infection, with or without chemotherapy, reinfection is a common phenomenon. Innovative and cost effective new drugs and combination therapies using new and old drug products are urgently needed. The development of broad-spectrum anti-parasitic agents able to be used in combination with existing chemotherapeutics is preferable to reduce the emergence of new resistance. An ideal anti-protozoal drug would target multiple protozoan parasites, be active by various routes of administration, reduce morbidity and mortality caused by such infections, not interfere with co-administered vaccines as they become available, and reduce the need for hospital-based treatment.

The important protozoal sources of infection addressed by the methods of treatment and compositions of the present invention are a subset of protozoal organisms within the biologic kingdom Protista. The protozoa relevant to the present invention are summarized in Table 1.

TABLE 1

Selected field of parasites relevant to treatment methods and compositions using DIM-related indoles.

| Phylum | Class | Order | Genus | Species |
|---|---|---|---|---|
|  | Microsporidia |  |  | *Enterocytozoon bieneusi* |
| Chromista |  |  |  |  |
|  | Bigyra |  |  | *Blastocystis hominis* |
| Parabasalia |  |  |  |  |
|  | Axostylata | Parabasalea | Trichomonadida | *Trichomonas vaginalis* |

TABLE 1-continued

Selected field of parasites relevant to treatment methods and compositions using DIM-related indoles.

| Phylum | Class | Order | Genus | Species |
|---|---|---|---|---|
| Euglenozoa | | | | |
| Subphylum Kinetoplasta | | | | |
| | Trypanosomatidea | Trypanosomatida | | |
| | | | Leishmania | |
| | | | | Leishmania species donovani, infantum (chagasi), tropica, braziliensis, guyanensis |
| | | | Trypanosoma | |
| | | | | Trypanosoma species Brucei, gambiense, rhodesiense |
| | | | | Trypanosoma cruzi |
| | | | | Trypanosoma rangeli |
| Apicomplexa (Sporozoa) | | | | |
| | Coccidea | | | |
| | | Adeleida | | |
| | | | | Cryptosporidium baileyi |
| | | | | Cryptosporidium meleagridis |
| | | | | Cryptosporidium parvum |
| | | | | Cryptosporidium muris |
| | | | | Cyclospora cayetanensis |
| | | | | Isospora belli |
| | | | Cystoisospora | |
| | | | | Cystoisospora |
| | | Eimeriida | | |
| | | | | Toxoplasma gondii |
| | | Haemosporida | | |
| | | | Plasmodium | |
| | | | | Plasmodium falciparum |
| | | | | Plasmodium malariae |
| | | | | Plasmodium ovale |
| | | | | Plasmodium vivax |
| | | | | Babesia gibsoni |
| | | | | Babesia microti |
| | | Conoidasida | | |
| | | | Eucoccidiorida | |
| | | | | Neospora |
| | | | | Sarcosystis homins |
| | | | | Suihominis, lindemanni |

2.2 Scope of Protozoal Parasitic Infections

Parasitic protozoa are responsible for a variety of human diseases transmitted by insect vectors, i.e., carriers, including malaria, leishmaniasis, and trypanosomiasis. Other protozoal parasites can be transmitted directly from other mammalian reservoirs or from person to person. Lacking vaccines, vector control and selective chemotherapy have been the only ways to reduce transmission and treat infected individuals, respectively. Because the immune system plays a crucial role in controlling protozoal infection, opportunistic infection with protozoal organisms is an increasing problem in infants, cancer patients, transplant recipients, and those co-infected with human immunodeficiency virus (HIV). Pregnancy also suppresses certain immune functions. New anti-protozal treatments are needed which are safer for mother and fetus during pregnancy, particularly for malaria, toxoplasmosis, and *trichomonas* infections. Vaccines are needed which overcome diminished immune responses and induce an adequate long term immune response. Vaccines can be used in conjunction with compatible chemotherapy to improve therapy of pre-existing chronic infection in endemic areas.

2.2.1 Malaria is an Uncontrolled Protozoal Disease

Malaria arises from infection with an Apicomplexan protozoan parasite known as *Plasmodium*. Only four species of the genus *Plasmodium* cause human malaria. *P. vivax* is the most common and fatal. *P. ovale* and *P. malariae* are less common and have intermediate severity. *P. falciparum* is the most virulent, responsible for high infant mortality, and associated with current drug resistance. The disease is transmitted to human beings through the bite of infected female *Anopheles* mosquitoes and by transfusion of infected blood.

Due to the emergence and spread of drug-resistant malaria parasites, pesticide-resistant malaria-transmitting mosquitoes, and population growth in endemic areas, malaria now causes approximately 500 million clinical cases per year. It is prevalent in children and pregnant women, causing about one million annual deaths in children under the age of five. Children growing up in rural and endemic areas are subject to more frequent malaria related illness and deaths than more resistant adults.

The most severe form of *Plasmodium falciparum* infection is cerebral malaria (CM). Cerebral malaria implies the presence of neurological features, especially impaired consciousness. Treatment of CM is limited to a few conventional anti-malarial drugs (quinine or artemisinins) and supportive care including parenteral fluids, blood exchange transfusion, osmotic diuretics and correction of hypoglycemia, acidosis and hypovolemia. The management of CM includes prompt administration of appropriate parenteral anti-malarial agents and early recognition and treatment of the complications. In children, the complications include severe anemia, seizures and raised intracranial pressure. In adults, renal failure and pulmonary edema are more common causes of death.

A number of drugs ranging from those of natural origin to synthetic ones have been developed for the treatment of malaria. Quinine and artemisinin are the commonly known drugs of natural origin, which are used for the treatment of malaria. A number of synthetic anti-malarial drugs such as chloroquine, mefloquine, primaquine, halofantrin, amodiaquine, proguanil, atovaquone, maloprim are known in the literature. Quinidine Gluconate, Quinine Sulfate, typically in combination with Doxycycline hyclate, Clindamycin, or Pyrimethamine-sufadoxine are also used for malaria. In chloroqine resistant strains, preferred oral therapy includes Mefloquine Hydrochloride and Atovaquone-proguanil hydrochloride combinations. In treatment of infections with *P. vivax, P. malariae, P. ovale*, and chloroquine sensitive *P. falciparum*, chloroquine phosphate and primaquine phosphate are used.

In recent years, drug resistant malaria has become one of the most serious problems in malaria control. Drug resistance necessitates the use of drugs which are more expensive and may have dangerous side effects. The emergence of resistance can be prevented by the use of combinations of drugs with different mechanisms of action. The use of drug combinations for all antimalarial treatment not only delays the onset of drug resistance, but also accelerates recovery and increases cure rates. A number of antimalarial combinations are already known in the field of malarial chemotherapy. The specific combinations in use, dosages, and relative merits of various combinations have been summarized (Kremsner et al., 2004, Lancet 364:285-94).

With the emergence of *P. falciparum* strains resistant to chloroquine and quinine, further alternative antimalarial chemotherapy is required. Due to frequent re-infection following complete or partial treatment, vaccine therapy promoting long term immunity to re-infection is needed. New chemotherapy will preferably clear the current infection and not interfere with co-administered vaccines as they become available. Preferred combinations of anti-malarials utilize drugs that overcome chloroquine resistance, have a good safety profile, and are well tolerated. Artemisinin, obtained from the plant *Artemisia anua*, and its derivatives are rapidly effective in severe malaria. Artemisinin compounds have been evaluated in several centers and are found to be effective, and safe (Miskra et al., 1995, Trans R Soc Trop Med Hyg 89:299-301).

In addition, the patent literature describes the combination of atovaquone and proguanil as a method for the treatment of malaria. See U.S. Pat. No. 5,998,449. The combination of fenozan with another anti-malarial agent selected from artemisinin, sodium artesunate, chloroquine, or mefloquine is described for the prophylactic and curative treatment of malaria. See U.S. Pat. No. 5,834,505. Synergistic combination kits using atemisinin derivatives, sulfadoxin and pyrimethamine for severe, multi-drug resistant malaria are described by Tipathi et al. in U.S. Patent Application Publication No. 2006/0141024 A1.

2.2.2 Trypanosomiasis Lacks Effective Chemotherapy for Early and Late Disease

African trypanosomiasis (sleeping sickness) is caused by a subspecies of the parasitic haemoflagellate, *Trypanosoma brucei*. The infection begins with the bite of an infected tsetse fly (*Glossina* spp.). Two forms of the disease are known, one caused by *Trypanosoma brucei rhodesiense*, endemic in Eastern and Southern Africa, and the other caused by *T. b. gambiense*, originally detected in West Africa, but also widespread in Central Africa. African Trypanosomiasis results in febrile, life-threatening illness in humans and also threatens livestock. *T. brucei* parasites rapidly invade the Central Nervous System (CNS) causing death within weeks if untreated. *T. b. gambiense* proliferates relatively slowly and can take several years before infecting the CNS system. There are four important drugs approved to treat these infections. Two of these, pentamidine and suramin, are used before the CNS involvement. The arsenic-based drug, melarsoprol is used in the case of infections established in the CNS. The fourth drug, eflornithine, is used against late stage infection caused by *T. b. gambiense*. This drug is ineffective against *T. b. rhodesiense*. Nifurtimox is another drug licensed for both American trypanosomiasis and melarsoprol-refractory late stage disease.

American trypanosomiasis or Chaga's disease is caused by *Trypanosoma cruzi* and effects millions of people in South and Central America, and Mexico. Untreated Chaga's disease causes decreased life expectancy due to parasitic cardiomyopathy and heart failure, megaesophagus, and megacolon. Blood-sucking triatomid bugs transmit the infection to young children and transplacental infection can occur with parasitemia during pregnancy. Nifurtimox and benznidazole are two drugs used for treatment of the acute disease, but are not known to be therapeutic for the chronic infection in older children and adults. In the absence of an effective vaccine, better agents are needed that can be taken prophylactically by at risk children. Following infection, additional agents are needed to be used in conjunction with nifurtimox and benznidazole to increase efficacy, permit lower doses of the current agents with reduced toxicity, and shorten the currently required duration of treatment.

2.2.3 Leishmaniasis Lacks Practical and Safe Chemotherapy

Human leishmaniasis comprises a heterogeneous spectrum of diseases. Three major forms are generally distinguished: cutaneous leishmaniasis, mucocutaneous leishmaniasis and visceral leishmaniasis, of which the latter is potentially lethal. They are caused by various species of the protozoan parasite *Leishmania* and transmitted by female sandflies. The disease is currently estimated to affect some 12 million people in 88 countries. Worldwide, *leishmania*/HIV co-infection is now considered an emerging disease where about 50% of adult visceral leishmaniasis cases are related to co-existing HIV infection.

The current treatment for leishmaniasis involves administration of pentavalent antimony complexed to a carbohydrate in the form of sodium stibogluconate (Pentosam or Sb(V)) or meglumine antimony (Glucantine), which are the only established anti-leishmanial chemotherapeutic agents with a clearly favorable therapeutic index. The exact chemical structure and mode of action of pentavalent antimonials is still uncertain. Amphotericin B and Pentamidine are the second line of anti-leishmanial agents, but are reserved for nonresponding infections due to potential toxicity. Since resistance to the antimony-based anti-Leishmanial drugs is emerging and treatment failures are common, new combination therapies are needed. Miltefosine is a recently introduced oral drug effective for visceral and cutaneous disease. The importance of this new oral agent extends to the treatment of dogs which serve as an important reservoir of the disease. The identification of additional, new and effective anti-leishmanial agents for oral administration would allow further treatment options, help prevent emerging resistance to Miltefosine and antimony-based drugs, and increase the chance for regional control of leishmaniasis. DIM has been shown to be a potent inhibitor of *Leishmania donovani* topoisomerase I (LdTOPILS) with an $IC_{50}$ of 1.2 µM. See Roy A., et al., Biochemical Journal, 8 Oct. 2007, Immediate Publication Manuscript BJ 20071286 (not the final version).

2.2.4 Trichomonal Disease

Trichomonal infection, typically vulvo-vaginitis in women and urethritis in men, is sexually acquired and one of the most common protozoal parasite infections in humans. In the United States, it is estimated that more than 2 million women are infected each year. *Trichomonas* vaginitis causes vulvar itching and an odorous vaginal discharge. It is caused by *Trichomonas vaginalis*, a single-celled protozoan parasite not normally found in the flora of the genitourinary tract. Typically Trichomonal infection is treated with oral metronidazole which is FDA approved in various dosage regimens. Though efficacious, Metronidazole can exhibit serious dose-related side effects, particularly on the blood and on the central nervous system. Experiments show it to be mutagenic and carcinogenic. Recently, treatment failure and emerging resistance to metronidizole have been documented, indicating a need for more consistently effective therapies which will include combinations of drugs active against strains of *T. vaginalis* that may be resistant to metronidazole. Preferred treatments will include agents safe for pregnant women and allow lower doses of co-administered metronidazole.

2.2.5 Protozoal Disease in Immunocompromised Hosts

The risk of parasitic diseases is also present outside developing countries and often takes the form of chronic diarrheal disease in subjects with underlying immune deficiency. These infections can be caused by *Isospora belli*, and *Cyclospora cayetanensis*, both coccidian protozoa, where infection results in self-limited diarrhea in normal hosts and prolonged diarrhea in individuals with AIDS. Both infections respond to treatment with timethroprim-sufamethoxazole. Cryptosporidia are additional coccidian parasites that cause diarrhea in animal species and humans. *Cryptosporidium parvum* and *C. Hominis* account for most coccidial infections in humans. These organisms form oocytes, which when digested release sporozoites that invade host epithelial cells, penetrating the cell membrane but not the enterocyte cytoplasm. Nitazoxanide is the only drug approved for the treatment of cryptosporidiosis in the United States. The identification of additional effective anti-crytosporidial agents for oral use would allow additional treatment options for individuals with HIV infection who respond unpredictably to Nitazoxanide.

Toxoplasmosis, is a zoonotic infection by the obligate intracellular protozoan, *Toxoplasma gondii*. Toxoplasmosis is found throughout the world, including the United States. Cats and other feline species are the natural hosts for *Toxoplasma gondii*, however tissue cysts (bradyzoites) have been recovered from all mammalian species examined. Pregnant women and those with weak immune systems are particularly susceptible to the health risks resulting from *Toxoplasma* infection. Severe toxoplasmosis, particularly trans-placental exposure, can result in damage to the brain, eyes, and other developing organs in utero. Currently available treatments for toxoplasmosis, which are the drugs trisulfa-pyrimdine, sulfadiazine and pyrimethamine, are not effective, and can be toxic to the host. Therefore, there is a need for therapeutic agents to treat toxoplasmosis that are more effective and less toxic than currently available treatment agents. No available agent is used to control Toxoplasmosis in cats.

2.3 Protozoal Cell Behavior Includes Apoptosis-Like Responses and Suppression of Apoptosis in Infected Host Cells Apoptosis is the process of programmed cell death by which damaged cells are eliminated upon generation of unopposed death signals within the damaged cell. While apoptosis is primarily viewed as a biologic response of multicellular organisms providing a means of eliminating infected or transformed cells in the setting of viral and cancer-related disease, protozoal organisms have also been noted to exhibit programmed cell death behavior (Lee et al., 2002, Cell Death Differ. 9:53-64). When infecting host cells in mammals, protozoal parasites have also been noted to suppress host cell apoptosis. For example, activation of the Nuclear Factor Kappa B (NFκB) survival signaling pathway has been described following infection by *Trypanosoma cruzi* (Petersen et al., 2006, Infect Immun. 74:1580-7).

2.4 Natural Indole Compounds can Influence Apoptosis

Cruciferous vegetables contain a family of plant protective compounds called glucosinolates which give rise to active compounds with indole rings exemplified by indole-3-carbinol (I3C). Oral ingestion of I3C results in the gastric conversion of I3C into at least twenty acid condensation products, many of which are bioavailable, the most prevalent of which include CTR (cyclic trimer; 5,6,11,12,17,18-hexahydrocyclonona[1,2-b:4,5-b':7,8-b' ]triindole), HI-IM (1-(3-hydroxymethyl)-indolyl-3-indolylmethane), DIM (diindolylmethane), ICZ (indolocarbazole) and LTr-1 (linear trimer; [2-(indol-3-ylmethyl)-indol-3-yl]indol-3-ylmethane) (Stresser et al., 1995, Drug Metabolism and Disposition 23:965-975). The fact that there are many non-DIM acid condensation products of I3C, produced in vivo at equal or greater levels as DIM, which can be responsible for I3C's activity, requires that biologic activities of individual condensation products like DIM be demonstrated directly.

As one of many products derived from I3C, DIM is also present in cruciferous plants following release of I3C. Once formed, DIM is stable in acid. In cell culture, isolated DIM has been shown to have apoptosis promoting effects in both estrogen-dependent and independent breast cancer cells (Hong et al., 2002, Biochem Pharmacol. 63:1085-97). In animals, orally administered DIM inhibits the growth of certain chemically induced forms of breast cancer (Chen et al., 1998, Carcinogenesis 19:1631-9). Recently, DIM has been shown to specifically induce apoptosis in Human Papilloma Virus (HPV) oncogene altered cervical cancer cell lines (Chen et al., 2001, J Nutr. 131:3294-3302). In further cell culture experiments, DIM has been shown to reduce activation of the NFκB signaling pathway in breast cancer cells (Rahman et al., 2005, Cancer Res. 65:364-71). Other non-DIM I3C condensation products were not tested. In vivo studies in mice suggest that expected effective plasma levels of DIM are not easily achieved in humans (Anderton et al., 2004, Drug Metab Dispos. 32:632-8).

In relation to its pro-apoptotic activity in tumor cells, DIM has also been shown to be estrogenic in breast cancer cells (Riby et al., 2000, Biochem. Pharmacol. 60:167-177) and in rainbow trout, a model of carcinogenesis relevant to cancer in humans (Shilling et al., 2001, Toxicology and Applied Pharmacology 170:191-200). Since estrogenic effects inhibit apoptosis, DIM may actually enhance estrogen related growth and survival of some cells. Based on the conflicting results of DIM's activity in cell culture studies and estrogenic activity in vivo, it is difficult to predict DIM's effects in vivo on protozoal disease processes. In addition, DIM has been shown to activate the Mitogen Activated Protein Kinase (MAPK) cell signaling pathway in cell culture (Leong et al., 2004, Mol Endocrinol. 18:291-302). Activated MAPK is associated with cancer promotion, cancer cell survival, and inhibition of apoptosis. These properties of DIM suggest that DIM would not be useful as a promoter of apoptosis in protozoal infection.

One approach, that has not been developed for protozoal parasitic disease, would be to selectively induce apoptosis in protozoal infected cells and tissues in order to cause the programmed death of parasites and of parasite infected cells. This would result in parasite clearance and increased apoptosis may support the development of protective host immunity.

3. SUMMARY OF THE INVENTION

The present invention relates to Diindolylmethane (DIM) and DIM-related indoles that are useful for the treatment and prevention or reducing the risk of protozoal diseases in mammals and birds. The present invention also relates to compositions comprising DIM-related indoles, optionally, in combination with one or more additional antiprotozoal agents. In certain embodiments, the compounds and methods of the present invention are used for treatment or prevention or reducing the risk of infections by the primary protozoal parasites affecting humans, including, but not limited to, hemoflagellates of the class Trypansomatidae, causing leishmaniasis and trypanosomiasis, flagellates of the class Axostylata causing Trichomonal infection, and parasites of the phylum, Apicomplexa, causing malaria, toxoplasmosis, cryptosporidiosis, and bebesiosis. Also covered by the methods are treatment of infections by fungi of the genus *Candida*, particularly *C. albicans*, which behave like intracellular protozoa by invading epithelial cells. In certain embodiments, the compounds and methods of the present invention are used for treatment or prevention or reducing the risk of infections affecting non-human mammals, including, but not limited to, protozoal parasitic diseases functionally related to malaria caused by parasites of the species *Neospora*. *Neospora* infections are known to occur in dogs, cattle, sheep, goats and horses. In certain embodiments, the compounds and methods of the present invention are used for treatment or prevention or reducing the risk of infections with species of *Coccidea*, also of the phylum Apicomplexa, which infect humans, domestic animals and livestock, including poultry, lambs, calves, piglets, and rabbits. As used herein, a subject includes, but is not limited to, humans, domestic animals such as dogs, and livestock such as poultry, sheep, lambs, piglets, rabbits, cattle, calves, goats and horses. In certain embodiments, the compounds and methods of the invention are used for the treatment or prevention or reducing the risk of infection caused by *Cyclospora, Isospora*, or *Blastocystis*.

In certain embodiments, the methods of the invention employ structurally-related, synthetically-derived, substituted diindolylmethane compounds referred to as DIM-related indoles to treat protozoal parasite infections. In a particular embodiments, the one or more DIM-related indoles of the invention are selected from the group consisting of 3,3'-diindolylmethane (DIM), hydroxylated DIMs, methoxylated DIMs, 2-(Indol-3-ylmethyl)-3,3'-diindolylmethane (LTR), hydroxylated LTRs, methoxylated LTRs, 5,5'-dimethylDIM (5-Me-DIM), 2,2'-dimethylDIM (2-Me-DIM), 5,5'-dichloroDIM (5-Cl-DIM), imidazolyl-3,3'-diindolylmethane, nitro-substituted imidazolyl-3,3'-diindolylmethanes, 2,10-dicarbethoxy-6-methoxy-5,7-dihydro-indolo-[2,3-b]carbazole, 6-ethoxycarbonyloxy-5,7-dihydro-indolo-[2,3-b]carbazole and 2,10-dicarbethoxy-6-ethoxycarbonyloxy-5,7-dihydro-indolo-[2,3-b]carbazole, and 2,6-dicarbethoxy-3,3'-dimethyl-13,14-diindolylmethane, and indole-3carbinol (I3C).

In certain embodiments the DIM-related indole or indoles are used in combination with anti-protozoal therapeutics. Anti-protozoal agents which are combined with DIM-related indoles according to the present invention include established antiprotozoal drugs, natural product derived antiprotozoal drugs, apoptosis promoting drugs often with a history of use as apoptosis promoting chemotherapeutics, and natural products from plants with antiprotozoal activity. Established antiprotozoal agents for combined use include atovaquone, amodiaquine, amphotericin, butoconazole, clindamycin, eflornithine, fumagillin, iodoquinol (diiodohydroxyquin), clioquinol (iodochlorhydroxyquin), Etanidazole, Benznidazole, fluoroquinolones, enoxacin, ciprofloxacin, doxycycline, melarsoprol, metronidazole, miltefosine, nifurtimox, nitazoxanide, paromomycin, pentamidine, sodium stibogluconate, suramin, tinidozole, pyrimethamine, proguanil (chloroguanide), spiramycin, and sulfadoxine. Natural product derived antiprotozoal drugs useful for combined use include sesquiterpene lactones related to artemisinin from *Artemisia annua*, particularly artemisinin, dihydroartemisinin, artemether, artesunate, and further derivatives of artemisinin, quinolines like quinine derived from the bark of the South American chinchona tree, including quinine and quinine-related quinolines, halofantrine, mefloquine, lumefantrine, amodiaquine, pyronaridine, piperaquine, chloroquine, hydryoxychloroquine, napthoquine, primaquine, and tafenoquine, curcuminoids derived from curcumin, an extract from *Curcuma domestica*, including 6-gingerol and 6-paradol, coronaridine, 18-methoxycoronaridine, selected flavonoids, including luteolin, extracts the fruit pericarp of *Sapindus mukorossi*, and extracts of *Yucca schidigera*. Apoptosis promoting antiprotozoal agents for combined use include artemisinin derivatives, atovaquone, chloroquine, iodoquinol (diiodohydroxyquin), clioquinol (iodochlorhydroxyquin), sodium stibogluconate, and curcumin. Some apoptosis promoting chemotherapeutics used are also useful in combination with DIM-related indoles and include Pyrroloquinazolinediamine, Novobiocin, cyclosporine, dihydrobetulinic acid, campothecins, especially topotecan, irinotecan, SN38 (the active metabolite of irinotecan), bortezimib, etoposide, salvicine, and doxorubicin. Antiprotozoal natural products useful with the methods of the present invention include teas and extracts made from *Artemisia annua*, teas and extracts made from *Curcuma domestica*, extracts from garlic which include allicin and other thiosulfinates, root extracts of *Uvaria chamae* (Annonaceae) and *Hippocratea Africana* (Hippocrateaceae), and root extracts of *Homalium letestui*. Preferred agents for combined use with DIM-related indoles include artemisinin extracts and related drugs, curcumin and curcumin-related drugs, and other antiprotozoal agents with short metabolic half lives. Specific, preferred antimalarials with rapid metabolism include artesunate, dihydroartemisinin, quinine, and clindamycin.

In a particular embodiment, the DIM-related indole and an antiprotozoal agent are administered simultaneously. In another embodiment, the DIM-related indole and antiprotozoal agent are administered within a short time of one another, for example, 30 seconds, 1 minute, 5 minutes, 15 minutes, 30 minutes, 1 hour, 4 hours, 8 hours, 12 hours or 24 hours of one another.

In an additional embodiment, the combination of a DIM-related indole and a antiprotozoal agent is administered in conjunction with a differentiation promoting agent which helps protozoa infected cells develop into more completely differentiated and therapeutically sensitive cells. Differentiation promoting agents include Vitamin-D, Vitamin-D derivatives, Vitamin-A (retinoids), 9-cis-Retinoic acid, 13-cis-Retinoic acid, trans-Retinoic acid, all-trans-Retinol, retinyl acetate, Retinyl palmitate, and granulcyte/macrophage colony stimulating factors including recombinant human Filgrastim and Sargramostim.

In an additional embodiment, the combination of a DIM-related indole and a antiprotozoal agent is administered in conjunction with anti-protozoal vaccines which contain attenuated protozoal organisms, typically inactivated by irradiation and/or chemical processing. Alternatively, the DIM-related indole, antiprotozoal agent, and anti-protozoal vaccine, are administered with an additional immune potentiating agent (which is not a DIM-related indole). Immune potentiating agents useful in the methods of the present invention include aloe vera extracts, purified aloe mannans and acemanans, mushroom extracts, beta-glucans, and extracts of the root of North American ginseng (*Panax quinquefolium*) containing poly-furanosyl-pyranosyl-saccharides (CV Technologies Inc., Edmonton). Beta-glucans include those derived from *Saccharomyces cerevisiae* (ImmunDyne, Inc., Florence, Ky.). Other useful fungal extracts containing branched glucans are derived from mushrooms, such as the maitake mushroom (*Grifola frondosa*).

The invention further provides compositions, for example, a composition comprising a therapeutically effective amount of the combination of DIM, or a DIM-related indole, and an anti-protozoal compound or combination of anti-protozoal compounds. In particular embodiments, the compositions are formulated for oral, sublingual, rectal, vaginal, parenteral, and topical administration. In a further particular embodiment, the different formulations are combined to form a kit combining rectal suppositories with an oral suspension for pediatric use, or rectal or vaginal suppositories with capsules or tablets for adult use.

The present invention also provides compositions for treating protozoal infections comprising DIM, a DIM-related indole, or DIM in combination with selected known antiprotozoal compounds, in an amount effective to reduce blood, tissue or intestinal parasite counts, formulated in the form of a dietary supplement, for example, a nutraceutical tablet, capsule, drink mix, or fortified food; a tea mix, or chewing gum.

In the methods and compositions of the invention, DIM or a DIM-related indole is preferably processed to increase bioavailablity and/or microencapsulated with phosphotidylcholine (PC), complexed with PC, or made into rapidly dissolving microparticles and nanoparticles. Preferably, the formulations will include specialized vehicles for rectal and vaginal administration and be safe for use during pregnancy.

4. DETAILED DESCRIPTION OF THE INVENTION

The present invention relates to Diindolylmethane and DIM-related indoles that are useful for the treatment and prevention or reducing the risk of protozoal diseases in mammals and birds. In particular, the invention relates to the treatment and prevention of the protozoal diseases in mammals and birds in Table 1. In certain embodiments, a DIM-related indole is used in combination with one or more of the following: an anti-protozoal agent, a differentiation agent, an immune potentiating agent and an anti-protozoal vaccine. The present invention is directed to compositions comprising a DIM-related indole, either alone or in combination with one or more additional antiprotozoal agents. The compounds and methods of the present invention may be used for treatment and control of infections by the primary protozoal parasites affecting man, including, but not limited to, hemoflagellates of the family Trypansomatidae, causing Leishmaniasis, Trypanosomiasis, and Bebesiosis, flagellates of the class Axostylata causing Trichomonal infection, and parasites of the Sporozoa phylum, Apicomplexa, causing malaria, toxoplasmosis, and cryptosporidiosis. Also covered by the methods are treatment of infections by fungi of the genus *Candida*, particularly *C. albicans*, which behave like intracellular protozoa by invading epithelial cells. In non-human mammals, protozoal parasitic disease functionally related to malaria includes disease caused by parasites of the species *Neospora*. *Neospora* infections are known to occur in dogs, cattle, sheep, goats and horses. Also treatable according to the methods and compositions of the present invention is infection with species of *Coccidea*, also of the phylum Apicomplexa, which infect humans, domestic animals and livestock, including poultry, lambs, calves, piglets, and rabbits.

Without being bound by any theory, it is believed that the compounds and methods of the present invention promote apoptosis, for example, by to inhibiting cell survival signaling in host cells where such signaling is a response protozoal parasite infection, which supports the induction of host immunity, especially when used in conjunction with anti-protozoal vaccines. Promotion of more efficient apoptosis and interaction of protozoal antigens with host immune cells is believed to result from the combined use of DIM-related indole with a variety of anti-protozoal agents, especially anti-protozoal vaccines.

Protozoal infection of cells initiates cell-growth and cell-survival mechanisms uniquely attributed to the interaction of protozoal parasite with host cell apoptotic mechanisms (Heussler et al., 2001, Int J Parasitol. 31:1166-76). Upon entry into cells, protozoal parasites provide an activation signal for cell survival including activation of NFκB signalling which inhibits cellular apoptosis (Shapira, 2004, J Parasitol. 34(3):393-400). In protozoal parasite infections, protozoal parasites utilize a variety of strategies to avoid interaction with the host immune system including differentiation to less activating forms, inhibition of pro-apoptotic stress proteins, and inhibition of immune activating antigen display on the surface of host cell membranes. DIM-related indoles trigger pro-apoptotic signals through endoplasmic reticulum stress which has been shown to induce apoptosis in cancerous cells (Sun et al., 2004, Cell Stress Chaperones. 9(1):76-87).

Without being bound by any theory, the present invention employs DIM-related indoles alone and together with additional antiprotozoal agents to inhibit the protozoal parasite associated activation of NFκB and selectively induce apoptosis in parasite infected cells, thereby reducing production of protozoal progeny, reducing parasite load, and resolving or shortening the period of infection. Prophylactic uses of DIM-related indoles alone or with antiprotozoal agents can prevent primary infection or re-infection with protozoal parasites. Selective inhibition of overactive survival and growth signals in protozoal parasite infected cells in the present invention can provide effective therapy, causing protozoa altered cells to be eliminated by triggering programmed cell death (apoptosis). Importantly, the promotion of apoptosis in protozoa infected cells can stimulate a more effective immune response, enhancing natural immunity and improving the short and long term benefit from co-administered anti-protozoal vaccines (James, 2005, J Infect Dis. 191(10):1573-5).

In certain embodiments, these methods of the present invention employ structurally-related, synthetically-derived, substituted diindolylmethane compounds administered orally, parenterally, vaginally, or per rectum. In a particular embodiment, a combination of DIM, or a DIM-related indole, and one or more known anti-protozoal agents are provided. The methods and compositions provide improved treatment for protozoal parasite infections.

The invention is based in part on expected additive and synergistic activity in using particular combinations of DIM-related indoles and antiprotozoal agents to selectively promote apoptosis in protozoal infected cells and apoptosis-like cell death in extracellular parasites. Combined use with DIM-related indole is believed to permit lower dose use of antiprotozoal agent(s), reducing dose-related side effects of these drugs. In certain embodiments, the compositions of the invention can be used with differentiation promoting agents such as Vitamin-D derivatives (calcitriol[1-alpha-25-dihydroxycholecalciferol]), retinoid derivatives (Vitamin-A, isotretinoin, retinoids), macrophage colony stimulating factors (Filgrastim and Sargramostim), and other immune potentiating agents. The combination of a DIM-related indole and antiprotozoal agents is believed to induce promotion of apoptosis resulting in the selective elimination of protozoa infected cells, and causes resolution of protozoal parasite related lesions of infected tissues, particularly the intestines, liver, skin, heart, spleen, and blood.

4.1 Diindolylmethane-Related Indoles

The DIM-related indoles or DIM compounds useful in the methods and compositions of the invention include DIM (3,3'-diindolylmethane) and the related linear DIM trimer (2-(indol-3-ylmethyl)-3,3'-diindolylmethane [also written: 2 (Indol-3-ylmethyl)-indol-3-yl]indol-3-ylmethane] (LTR), and Indole-3-Carbinol (I3C). As used herein, "DIM-related compound", "DIM-related indole", and "DIM derivative" are used interchangeably, and refer to both natural metabolites and analogs of DIM, and also to "structurally-related, synthetically-derived, substituted diindolylmethane compounds" and "synthetic derivatives of DIM", such as those disclosed herein and known in the art. As used herein, "cruciferous-related indoles" encompasses the terms "DIM-related compound", "DIM-related indole", and "DIM derivative". One of ordinary skill in the art will recognize that in any of the pharmaceutical compositions or methods of the invention where DIM is used, a DIM-related compound, including a structurally-related, synthetically-derived, substituted diindolylmethane compound or synthetic derivative of DIM, can be used.

The chemical structure of a DIM is as follows (where each of the R groups is H):

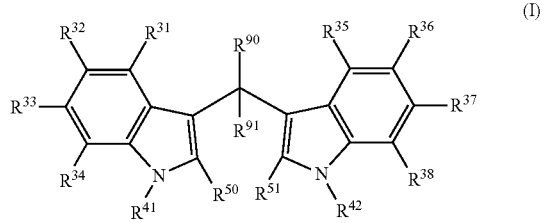

(I)

In particular embodiments, the DIM-related indole is a compound of formula I, wherein $R^{42}$, $R^{51}$, $R^{35}$, $R^{36}$, $R^{37}$, $R^{38}$, $R^{90}$, $R^{41}$, $R^{50}$, $R^{31}$, $R^{32}$, $R^{33}$, $R^{34}$ and $R^{91}$ individually and independently, are hydrogen or a substituent selected from the group consisting of a halogen, a hydroxyl, a nitro, —$OR^{100}$, —CN, —$NR^{100}R^{101}$, —$NR^{100}R^{101}R^{102+}$, —$COR^{100}$, $CF_3$, —$S(O)nR^{100}$ (n=0-2), —$SO_2NR^{100}R^{101}$, —$CONR^{100}R^{101}$, —$NR^{100}COR^{101}$, —$NR^{100}C(O)NR^{101}R^{102}$, —$P(O)(OR^{100})_n$ (n=1-2), optionally substituted alkyl, halovinyl, alkenyl, alkynyl, aryl, heteroalkyl, heteroaryl, or optionally substituted cycloalkyl or cycloakenyl, all of one to ten carbons and optionally containing 1-3 heteroatoms O or N, wherein $R^{100}$, $R^{101}$ and $R^{102}$ are optionally substituted alkyl, alkenyl, alkynl, aryl, heteroalkyl, heteroaryl of one to ten carbons, and $R^{90}$ and $R^{91}$ may further be O to create a ketone. In particular embodiments, the compound includes at least one such substituent, preferably at a position other than, or in addition to $R^{42}$ and $R^{41}$, the linear or branched alkyl or alkoxy group is one to five carbons, and/or the halogen is selected from the group consisting of chlorine, iodine, bromine and fluorine.

In certain embodiments, an active hydroxylated or methyoxylated metabolite of DIM, i.e., a compound of formula I, wherein $R^{32}$, $R^{33}$, $R^{36}$, and $R^{37}$ are substituents independently selected from the group consisting of hydrogen, hydroxyl, and methoxy, and $R^{31}$, $R^{34}$, $R^{35}$, $R^{38}$, $R^{41}$, $R^{42}$, $R^{50}$, and $R^{51}$ are hydrogen, is utilized. In particular embodiments, the DIM-related indole is a mono- or di-hydroxylated DIM derivatives at carbon positions 2, 4-7 and 2', and 4'-7', including each of [2, 4, 5, 6 or 7]-monohydroxy-DIM or [2', 4', 5', 6' or 7']-monohydroxy-DIM (e.g. 2-hydroxy-DIM, 4-hydroxy-DIM, etc.); and each of [2, 4, 5, 6 or 7], [2, 4, 5, 6 or 7]-dihydroxy-DIM, [2', 4', 5', 6' or 7'], [2', 4', 5', 6' or 7']-dihydroxy-DIM, or [2, 4, 5, 6 or 7], [2', 4', 5', 6' or 7']-dihydroxy-DIM (e.g. 2,4-dihydroxy-DIM, 2,5-dihydroxy-DIM etc, 2,2'-dihydroxy-DIM, 2,4'-dihydroxy-DIM etc.); particularly bilaterally symmetrical species, such as 2,2'-dihydroxy-DIM.

In particular embodiments, the indolyl moieties are symmetrically substituted, wherein each moiety is similarly mono-, di-, tri-, para-, etc. substituted. In other particular embodiments, $R^{42}$, $R^{51}$, $R^{35}$, $R^{37}$, $R^{38}$, $R^{90}$, $R^{41}$, $R^{50}$, $R^{31}$, $R^{33}$, $R^{34}$ and $R^{91}$ are hydrogen, and $R^{36}$ and $R^{32}$ are a halogen selected from the group consisting of chlorine, iodine, bromine and fluorine. Representative compounds include, but are not limited to, 3,3'-diindolylmethane, 5,5'-dichloro-diindolylmethane; 5,5'-dibromo-diindolylmethane; and 5,5'-difluoro-diindolylmethane. Additional preferred such DIM derivatives include compounds wherein $R^{42}$, $R^{51}$, $R^{35}$, $R^{37}$, $R^{38}$, $R^{90}$, $R^{41}$, $R^{50}$, $R^{31}$, $R^{33}$, $R^{34}$ and $R^{91}$ are hydrogen, and $R^{36}$ and $R^{32}$ are an alkyl or alkoxyl having from one to ten carbons, and most preferably one to five carbons. Representative compounds include, but are not limited to, 5,5'-dimethyl-diindolylmethane, 5,5'-diethyl-diindolylmethane, 5,5'-dipropyl-diindolylmethane, 5,5'-dibutyl-diindolylmethane, 5,5'-dipentyl-diindolylmethane, 5,5'-dimethoxy-diindolylmethane, 5,5'-diethoxy-diindolylmethane, 5,5'-dipropyloxy-diindolylmethane, 5,5'-dibutyloxy-diindolylmethane, and 5,5'-diamyloxy-diindolylmethane.

Additional preferred DIM derivatives include compounds wherein $R^{51}$, $R^{35}$, $R^{36}$, $R^{37}$, $R^{38}$, $R^{90}$, $R^{50}$, $R^{31}$, $R^{32}$, $R^{33}$, $R^{34}$ and $R^{91}$ are hydrogen, and $R^{42}$ and $R^{41}$ are an alkyl or alkoxyl having from one to ten carbons, and most preferably one to five carbons. Representative compounds include, but are not limited to, N,N'-dimethyl-diindolylmethane, N,N'-diethyl-diindolylmethane, N,N'-dipropyl-diindolylmethane, N,N'-dibutyl-diindolylmethane, and N,N'-dipentyl-diindolylmethane. In yet another embodiment, $R^{42}$, $R^{35}$, $R^{36}$, $R^{37}$, $R^{38}$, $R^{90}$, $R^{41}$, $R^{31}$, $R^{32}$, $R^{33}$, $R^{34}$ and $R^{91}$ are hydrogen, and $R^{51}$ and $R^{50}$ are alkyl of one to ten carbons, and most preferably one to five carbons. Representative compounds include, but are not limited to, 2,2'-dimethyl-diindolylmethane, 2,2'-diethyl-diindolylmethane, 2,2'-dipropyl-diindolylmethane, 2,2'-dibutyl-diindolylmethane, and 2,2'-dipentyl-diindolylmethane. In another embodiment, $R^{42}$, $R^{51}$, $R^{35}$, $R^{37}$, $R^{38}$, $R^{90}$, $R^{41}$, $R^{50}$, $R^{31}$, $R^{33}$, $R^{34}$ and $R^{91}$ are hydrogen, and $R^{36}$ and $R^{32}$ are nitro.

In an alternative embodiment, active DIM derivatives with $R_{32}$ and $R_{36}$ substituents made up of ethoxycarbonyl groups, and $R_{50}$, $R_{51}$ are either hydrogen or methyl, are utilized.

In another embodiment, active substituted DIM derivatives including methylated and chlorinated compounds, exemplified by those that include 5,5'-dimethylDIM (5-Me-DIM), 2,2'-dimethylDIM (2-Me-DIM), and 5,5'-dichloroDIM (5-Cl-DIM) are described in U.S. Patent Application Publication No. 20020115708 by Safe, published Aug. 22, 2002, incorporated herein by reference in its entirety, are utilized in the present invention. In another embodiment, active DIM derivatives include imidazolelyl-3,3'-diindolylmethane, including nitro substituted imidazolelyl-3,3'-diindolylmethanes, and additional DIM-related compounds described in U.S. Patent Application Publication No. 2004/0043965 by Jong, Ling, published Mar. 4, 2004, incorporated herein by reference in its entirety, are utilized. In a further embodiment, active DIM derivatives described in U.S. Pat. No. 6,656,963, U.S. Pat. No. 6,369,095 and U.S. Patent Application Publication No. 20060229355 by Bjeldanes et al., published Oct. 12, 2006, incorporated herein by reference in its entirety, are utilized.

The chemical structure of LTR is as follows (where each of the R groups is H):

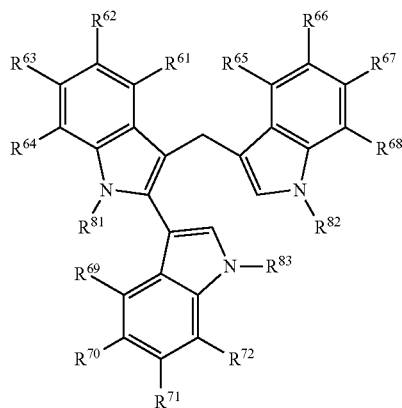

In certain embodiments, an active hydroxylated or methyoxylated metabolite of LTR, i.e., a compound of formula II, wherein $R^{62}$, $R^{63}$, $R^{66}$, $R^{67}$, $R^{70}$, and $R_{71}$ are substituents independently selected from the group consisting of hydrogen, hydroxyl, and methoxy, and $R^{61}$, $R^{64}$, $R^{65}$, $R^{68}$, $R^{69}$, $R^{72}$, $R^{81}$, $R^{82}$, and $R^{83}$ are hydrogen, is utilized.

In certain embodiments, a DIM related compound has formula (III):

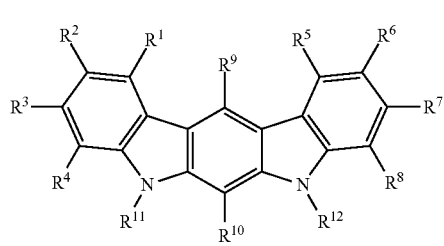

wherein:

$R^1$, $R^2$, $R^3$, $R^4$, $R^5$, $R^6$, $R^7$, $R^8$, $R^9$, and $R^{10}$ are substituents independently selected from the group consisting of hydrogen, $C_1$-$C_{24}$ alkyl, $C_2$-$C_{24}$ alkenyl, $C_2$-$C_{24}$ alkynyl, $C_5$-$C_{20}$ aryl, $C_6$-$C_{24}$ alkaryl, $C_6$-$C_{24}$ aralkyl, halo, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl, acyloxy, $C_2$-$C_{24}$ alkoxycarbonyl, $C_6$-$C_{20}$ aryloxycarbonyl, halocarbonyl, $C_2$-$C_{24}$ alkylcarbonato, $C_6$-$C_{20}$ arylcarbonato, carboxy, carboxylato, carbamoyl, mono-($C_1$-$C_{24}$ alkyl)-substituted carbamoyl, di-($C_1$-$C_{24}$ alkyl)-substituted carbamoyl, mono-substituted arylcarbamoyl, thiocarbamoyl, carbamido, cyano, isocyano, cyanato, isocyanato, isothiocyanato, azido, formyl, thioformyl, amino, mono- and di-($C_1$-$C_{24}$ alkyl)-substituted amino, mono- and di-($C_5$-$C_{20}$ aryl)-substituted amino, $C_2$-$C_{24}$ alkylamido, $C_6$-$C_{20}$ arylamido, imino, alkylimino, arylimino, nitro, nitroso, sulfo, sulfonato, $C_1$-$C_{24}$ alkylsulfanyl, arylsulfanyl, $C_1$-$C_{24}$ alkylsulfinyl, $C_5$-$C_{20}$ arylsulfinyl, $C_1$-$C_{24}$ alkylsulfonyl, $C_5$-$C_{20}$ arylsulfonyl, phosphono, phosphonato, phosphinato, phospho, phosphino, and combinations thereof, and further wherein any two adjacent (ortho) substituents may be linked to form a cyclic structure selected from five-membered rings, six-membered rings, and fused five-membered and/or six-membered rings, wherein the cyclic structure is aromatic, alicyclic, heteroaromatic, or heteroalicyclic, and has zero to 4 non-hydrogen substituents and zero to 3 heteroatoms; and $R^{11}$ and $R^{12}$ are independently selected from the group consisting of hydrogen, $C_1$-$C_{24}$ alkyl, $C_2$-$C_{24}$ alkoxycarbonyl, amino-substituted $C_1$-$C_{24}$ alkyl, ($C_1$-$C_{24}$ alkylamino)-substituted $C_1$-$C_{24}$ alkyl, and di-($C_1$-$C_{24}$ alkyl)amino-substituted $C_1$-$C_{24}$ alkyl, with the provisos that: at least one of $R^1$, $R^2$, $R^3$, $R^4$, $R^5$, $R^6$, $R^7$, $R^8$, $R^9$, $R^{10}$, $R^{11}$ and $R^{12}$ is other than hydrogen; and when $R^1$, $R^2$, $R^3$, $R^4$, $R^5$, $R^6$, $R^7$, and $R^8$ are selected from hydrogen, halo, alkyl and alkoxy, then $R^{11}$ and $R^{12}$ are other than hydrogen and alkyl.

A preferred embodiment includes the use of 2,10-dicarbethoxy-6-methoxy-5,7-dihydro-indolo-[2,3-b]carbazole (SRI13668 (SRI Inc., Menlo Park, Calif.)). Additional preferred embodiments include the use of 6-ethoxycarbonyloxy-5,7-dihydro-indolo-[2,3-b]carbazole and 2,10-dicarbethoxy-6-ethoxycarbonyloxy-5,7-dihydro-indolo-[2,3-b]carbazole (SRI Inc., Menlo Park, Calif.).

In another embodiment, a DIM related compound has formula (IV):

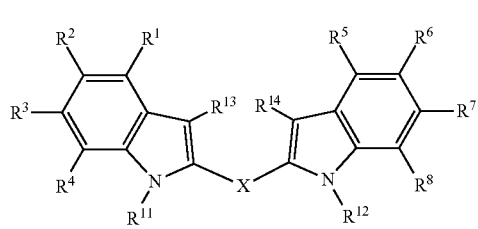

wherein:

$R^1$, $R^2$, $R^3$, $R^4$, $R^5$, $R^6$, $R^7$, and $R^8$ are substituents independently selected from the group consisting of hydrogen, $C_1$-$C_{24}$ alkyl, $C_2$-$C_{24}$ alkenyl, $C_2$-$C_{24}$ alkynyl, $C_5$-$C_{20}$ aryl, $C_6$-$C_{24}$ alkaryl, $C_6$-$C_{24}$ aralkyl, halo, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl, acyloxy, $C_2$-$C_{24}$ alkoxycarbonyl, $C_6$-$C_{20}$ aryloxycarbonyl, halocarbonyl, $C_2$-$C_{24}$ alkylcarbonato, $C_6$-$C_{20}$ arylcarbonato, carboxy, carboxylato, carbamoyl, mono-($C_1$-$C_{24}$ alkyl)-substituted carbamoyl, di-($C_1$-$C_{24}$ alkyl)-substituted carbamoyl, mono-substituted arylcarbamoyl, thiocarbamoyl, carbamido, cyano, isocyano, cyanato, isocyanato, isothiocyanato, azido, formyl, thioformyl, amino, mono- and di-($C_1$-$C_{24}$ alkyl)-substituted amino, mono- and di-($C_5$-$C_{20}$ aryl)-substituted amino, $C_2$-$C_{24}$ alkylamido, $C_5$-$C_{20}$ arylamido, imino, alkylimino, arylimino, nitro, nitroso, sulfo, sulfonato, $C_1$-$C_{24}$ alkylsulfanyl, arylsulfanyl, $C_1$-$C_{24}$ alkylsulfinyl, $C_5$-$C_{20}$ arylsulfinyl, $C_1$-$C_{24}$ alkylsulfonyl, $C_5$-$C_{20}$ arylsulfonyl, phosphono, phosphonato, phosphinato, phospho, phosphino, and combinations thereof, and further wherein any two adjacent (ortho) substituents may be linked to form a cyclic structure selected from five-membered rings, six-membered rings, and fused five-membered and/or six-membered rings, wherein the cyclic structure is aromatic, alicyclic, heteroaromatic, or heteroalicyclic, and has zero to 4 non-hydrogen substituents and zero to 3 heteroatoms, with the proviso that one but not both of $R^2$ and $R^6$ is amino, mono-substituted amino, or di-substituted amino;

$R^{11}$ and $R^{12}$ are independently selected from the group consisting of hydrogen, $C_1$-$C_{24}$ alkyl, $C_2$-$C_{24}$ alkoxycarbonyl, amino-substituted $C_1$-$C_{24}$ alkyl, ($C_1$-$C_{24}$ alkylamino)-substituted $C_1$-$C_{24}$ alkyl, and di-($C_1$-$C_{24}$ alkyl)amino-substituted $C_1$-$C_{24}$ alkyl;

$R^{13}$ and $R^{14}$ are defined as for $R^1$, $R^2$, $R^3$, $R^4$, $R^5$, $R^6$, $R^7$, and $R^8$, with the proviso that at least one of $R^{13}$ and $R^{14}$ is other than hydrogen; and X is O, S, arylene, heteroarylene, $CR^{15}R^{16}$ or $NR^{17}$ wherein $R^{15}$ and $R^{16}$ are hydrogen, $C_1$-$C_6$ alkyl, or together form $=CR^{18}R^{19}$ where $R^{18}$ and $R^{19}$ are hydrogen or $C_1$-$C_6$ alkyl, and $R^{17}$ is as defined for $R^{11}$ and $R^{12}$.

A preferred embodiment includes the use of 2,6-dicarbethoxy-3,3'-dimethyl-13,14-diindolylmethane (SRI Inc., Menlo Park, Calif.).

In another embodiment, a DIM related compounds has formula (V):

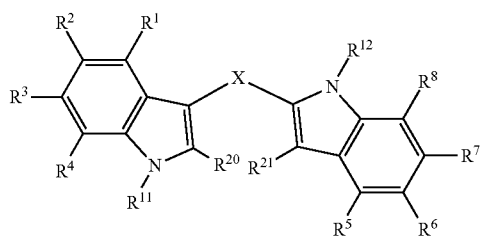

(V)

wherein:

$R^1$, $R^2$, $R^3$, $R^4$, $R^5$, $R^6$, $R^7$, $R^8$, $R^{11}$, $R^{12}$, and X are defined as for compounds of formula (III); and $R^{20}$ and $R^{21}$ are defined as for $R^1$, $R^2$, $R^3$, $R^4$, $R^5$, $R^6$, $R^7$, and $R^5$.

In yet another embodiment, the DIM-related indole is an indole-3-carbinol tetrameric derivative (Brandi et al., 2003, Cancer Res. 63:4028-4036). In a further embodiment the DIM-related indole is an indole-3-carbinol derivative described as an antitumor agent (Weng J R, Tsai C H, Kulp S K, Wang D, Lin C H, Yang H C, Ma Y, Sargeant A, Chiu C F, Tsai M H, Chen C S. A potent indole-3-carbinol derived antitumor agent with pleiotropic effects on multiple signaling pathways in prostate cancer cells. Cancer Res. 2007 Aug. 15; 67(16):7815-24).

Substituted DIM analogs are readily prepared by condensation of formaldehyde with commercially available substituted indoles. Precursor compounds can be synthesized by dimethylformamide condensation of a suitable substituted indole to form a substituted indole-3-aldehyde. Suitable substituted indoles include indoles having substituents at $R^{42}$, $R^{51}$, $R^{35}$, $R^{36}$, $R^{37}$ and $R^{38}$ positions. These include, but are not limited to 5-methoxy, 5-chloro, 5-bromo, 5-fluoro, 5'-methyl, 5-nitro, n-methyl and 2-methyl indoles. The substituted indole 3-aldehyde product is treated with a suitable alcohol such as methanol and solid sodium borohydride to reduce the aldehyde moiety to give substituted I3Cs. Substituted DIMs are prepared by condensing the substituted indole-3-carbinol products. This may be achieved, for example, by treatment with a phosphate buffer having a pH of around 5.5-7.4.

4.2 Combination Therapy

In certain embodiments of the invention, a DIM-related indole may be used in combination with one or more of the following: an anti-protozoal agent, a differentiation agent, an immune potentiating agent or an anti-protozoal vaccine. It is understood that more than one agent from each class can be used, for example, multiple anti-protozoal agents.

Particularly preferred drug combinations to be used in conjunction with additional DIM-related indoles according to the present invention include the non-artemisinin combinations quinine and sulfadoxine-pyrimethamine and quinine and doxycycline. Artemisinin based combination treatments to be used with DIM-related indoles include Artemether-lumefantine, artesunate and amodiaquine, dihydroartemisinin and piperaquine, atresunate and mefloquine, artesunate and sulfadoxine-pyrimetamine, and dihydroartemisinin-napthoquine-trimethoprim. For crytosporidial infections DIM-related indole, artemisinin and curcumin or genistein are a preferred combinations. For Trichomonal infections a DIM-related indole is used with artesunate, metronidazole, tinidazole, or hexadecylphosphocholine (miltefosine). For Candidal infections a DIM-related indole is used with an azole derivative, particularly an imidizole compound like clotrimizole, miconazole, or butoconazole. For combined bacterial and Trichomonal vaginitis, a DIM-related indole is used in combination with clindamycin, or with both clindamycin and artesunate. Alternatively, multi-organism infection can be treated with a DIM-related indole combined with metronidazole, or with both metrodidazole and artesunate.

4.2.1 Anti-Protozoal Agents

Anti-protozoal agents which can be combined with DIM-related indoles according to the present invention include established antiprotozoal drugs, natural product derived antiprotozoal drugs, apoptosis promoting drugs often with a history of use as apoptosis-promoting chemotherapeutics, and known antiprotozoal natural products. As used herein, an "anti-protozoal agent" does not include a DIM-related indole (which has anti-protozoal activity). In other words, in referring to the combination of a DIM-related indole and an anti-protozoal agent, the "anti-protozoal agent" is an agent other than a DIM-related indole.

Antiprotozoal agents include, but are not limited, atovaquone; diaminopyrimidines, especially amodiaquine, amphotericin, butoconazole, astemizole clindamycin, eflornithine, fumagillin; the 8-hydroxyquinolines, iodoquinol (diiodohydroxyquin), clioquinol (iodochlorhydroxyquin), the 2-nitroimidazoles, Etanidazole, Benznidazole fluoroquinolones, enoxacin, ciprofloxacin; doxycycline, melarsoprol, metronidazole, tinidazole, miltefosine, nifurtimox, nitazoxanide, paromomycin, pentamindine, sodium stibogluconate, antimony gluconate (SAG), and related antimonials, suramin, including the sodium salt, tinidazole, pyrimethamine, proguanil (chloroguanide), spiramycin, and sulfadoxine. Also useful are detergent and non-detergent spermacides that have additional anti-protozoal activity when used in topical formulations (Gupta G. Microbicidal spermicide or spermicidal microbicide?Eur J Contracept Reprod Health Care. 2005 December; 10(4):212-8).

Natural product derived antiprotozoal drugs include, but are not limited to, sesquiterpene lactones related to artemisinin from *Artemisia annua*, particularly artemisinin, dihydroartemisinin, artemether, artesunate, and further derivatives of artemisinin described in the literature (Haynes, 2006, From artemisinin to new artemisinin antimalarials: biosynthesis, extraction, old and new derivatives, stereochemistry and medicinal chemistry requirements. Curr Top Med Chem. 6(5):509-37); quinolines like quinine derived from the bark of the South American chinchona tree, including alkaloids structurally related to quinine, quinine and quine-related quinolines, halofantrine, mefloquine, lumefantrine, amodiaquine, pyronaridine, piperaquine, chloroquine, hydryoxychloroquine, napthoquine, primaquine, tafenoquine, amodiaquine and 4-aminoquinolines derived from the quinolines (Neill et al., 2006, Curr Top Med Chem. 6:479-507); other quinones including those extracted from *Salvia prionitis*, particularly salvicine and its derivatives (Qing C. et al, In vitro cytotoxicity of a salvicine, a novel diterpenoid quinone, Zhongguo Yao Li Xue Bao. 1999 April; 20(4):297-302); curcuminoids derived from curcumin, extracted from *Curcuma domestica*, including 6-gingerol and 6-paradol (Surh et al., 1999, J Environ Pathol Toxicol Oncol. 18:131-9); selected flavonoids and isoflavones, including, but not limited to, Genistein from soy, and derivatives from a number of plant sources including dehydrosilybin, silybin A and silybin B and isosilybin A and isosilybin B, and 8-(1;1)-DMA-kaempferide (Tasdemir et al., 2006, Antimicrob Agents Chemother. 50:1352-64), luteolin, baicalein, dihydrobetulinic acid, quercetin, eriodictyol acid, lursolic acid, oleanolic acid; and triterpenes, particularly Ganoderic acid X, isolated from *Ganoderma amboinense* and triterpene rich extracts of *Sapindus mukorossi* known to have anti-trichomonal activity.

Apoptosis promoting antiprotozoal agents include, but are not limited to, artemisinin derivatives, atovaquone, chloroquine, iodoquinol (diiodohydroxyquin), clioquinol (iodochlorhydroxyquin), Jasmonic acid [3-oxo-2-(2-pentenyl)cyclopentaneacetic acid], methyl jasmonate[methyl 3-oxo-2-(2-pentenyl)cyclopentaneacetic acid], and cis-jasmone[3-methyl-2-(2-pentenyl)-2-cyclopenten-1-one], 3,3'-dihexyloxacarbocyanine iodide, sodium stibogluconate, extracts of *Yucca schidigera*, and curcumin. Apoptosis promoting chemotherapeutics include, but are not limited to, Pyrroloquinazolinediamine, Novobiocin, quercetin, cyclosporine, dihydrobetulinic acid, campothectins, especially topotecan, irinotecan, SN38 (the active metabolite of irinotecan), bortezimib, etoposide, quinones including salvicine, and anthracyclines including doxorubicin, daunorubicin, 4'-epirubicin, idarubicin, and deoxydoxorubicin.

Antiprotozoal natural products include, but are not limited to, teas and extracts made from *Artemisia annua*, teas and extracts made from *Curcuma domestica*, extracts from garlic which include allicin and other thiosulfinates, root extracts of *Uvaria chamae* (Annonaceae) and *Hippocratea Africana* (Hippocrateaceae), and root extracts of *Homalium letestui*. Also useful are extracts of Brasilian plants with demonstrated anti-malarial activity, including *Vernonia brasiliana* and *Acanthospermum australe* (Carvalho, 1991, Braz J Med Biol Res. 24(11):1113-23, and Botsaris A S. Plants used traditionally to treat malaria in Brazil: the archives of Flora Medicinal. J Ethnobiol Ethnomed. 2007 May 1; 3:18).

Preferred agents for combined use with DIM-related indoles include artemisinin extracts and related drugs, curcumin and curcumin-related drugs, and other antiprotozoal agents with short metabolic half lives, preferably with a half-life similar to DIM (i.e., approximately 2-7 hours). In use with DIM-related indoles preferred antimalarials will be metabolically cleared within 12 hours following an oral dose and not increase activity of drug metabolizing cytochrome enzymes (Giao et al., 2001, Clin Pharmacokinet. 40(5):343-73). Additional useful natural product preparations are described in the literature (Willcox et al., 2004, BMJ. 329(7475):1156-9).

4.2.2 Differentiation Promoting Agents

In an additional embodiment, the combination of a DIM-related indole and a known antiprotozoal agent is administered in conjunction with differentiation promoting agents which help protozoa infected cells develop into more completely differentiated and more therapeutically sensitive cells. Differentiation promoting agents include Vitamin-D, Vitamin-D derivatives, Vitamin-A (retinoids), retinoid derivatives, and granulocyte/macrophage colony stimulating factors including recombinant human Filgrastim and Sargramostim.

4.2.3 Immune Potentiating Agents

The DIM-related indoles can also be used in combination with non-DIM related indole immune potentiating agents. Immune potentiating agents useful in the methods of the present invention include Aloe vera extracts, mushroom extracts, beta-glucans, and extracts of the root of North American ginseng (*Panax quinquefolium*) containing poly-furanosyl-pyranosyl-saccharides (CV Technologies Inc., Edmonton). Useful *Panax quinquefolium* extracts are described in U.S. Pat. No. 6,083,932 by Pang et al. which is herein incorporated by reference in its entirety. Beta-glucans include those derived from *Saccharomyces cerevisiae* (En-Bio Technology Co., Ltd.). Other useful fungal extracts containing branched glucans are derived from mushrooms, such as the maitake mushroom (*Grifola frondosa*). Oral use of beta-glucans in infections has been described (Jung et al., 2004, J Vet Med B Infect Dis Vet Public Health. 51(2):72-6).

4.2.4 Anti-Protozoal Vaccines

Existing vaccines do not induce sufficient protective immunity to clear existing infection and prevent a repeat infection. Therefore, in one aspect of the invention, a DIM related indole is administered with a vaccine to improve the response to the vaccine, i.e., by inducing a greater response through inducing apoptosis.

In one embodiment, a DIM-related indole, optionally with an antiprotozoal agent, is administered in conjunction with an anti-protozoal vaccine, for example, a vaccine which contains attenuated protozoal organisms, typically inactivated by irradiation and/or chemical processing. Promotion of more efficient apoptosis of host cells infected with attenuated protozoa and more effective interaction of protozoal antigens with host immune cells is believed to result from the combined use of DIM-related indole with a variety of vaccines.

4.3 Prevention and Treatment of Protozoal Parasite Infections

In certain embodiments, the present invention provides for the prevention and treatment of protozoal parasite infections which include active infections and asymptomatic chronic infections. Currently, this spectrum of protozoal parasite infections lacks adequate and effective therapy due to failure of previous approaches to selectively eliminate protozoal parasite infected cells and tissues and to target the anti-apoptotic cell signaling pathways activated by protozoal parasites. Ideally, use of DIM-related indoles will allow safer and more effective treatments of protozoal infections during pregnancy in immune compromised patients. Treatment of the various protozoal parasitic diseases varies according to the parasite type and setting for treatment.

4.3.1 General Principles of Treatment for Protozoal Parasites Using DIM-Related Indoles DIM-related indoles are used for the treatment and prevention of protozoal parasite infections in formulations most suitable for the disease entity, disease severity, and setting of treatment. An objective of the invention is to eliminate or shorten the need for parenteral therapy of protozoal diseases and, in doing so, reduce the need for hospitalization. When appropriate DIM is used in combination with other desirable antiprotozoal agents to reduce the chance of selecting for resistance to DIM-related indole activity. Desirable antiprotozoal agents for combined use possess one or more of the following important characteristics: safety, stability, chemical computability in formulations, tolerability, effectiveness, oral or intravenous dosage form, short elimination half-time, independent mode of action, synergistic activity in vivo. Ideally, agents for combination will have low cost and allow a short duration of use in order to achieve durable treatment response, and be appropriate for both adult and pediatric use.

Also important in combined uses and products is compatibility with use in conjunction with antiprotozoal vaccines, including those which may be developed in the future. Desirable antiprotozoal agents for combined use include compounds which like DIM-related indoles support selective apoptosis of parasite infected cells. Examples include, but are not limited to, artemisinin derivatives, atovaquone, chloroquine, iodoquinol (diiodohydroxyquin), clioquinol (iodochlorhydroxyquin), miltefosine, sodium stibogluconate, and curcumin.

Also desirable for use in combination with DIM-related indoles, with or without vaccines, are selected antibiotic or chemotherapeutic agents which promote apoptosis. Desirable agents inhibit proteosomal function, induce endoplasmic reticulum stress, inhibit topoisomerase enzymes, inhibit vacuolar-$H^+$-ATPase, and/or inhibit farnesyl transferase enzymes. Preferred chemotherapeutic agents for use in combination with DIM-related indoles for protozoal parasites are fluoroquinolones, enoxacin, ciprofloxacin, Novobiocin, cyclosporine, luteolin, butoconazole, sodium butyrate (Sodium butanoate), phenylbutryate, curcumin, evodiamine, dihydrobetulinic acid, campothecins, especially topotecan, irinotecan, bortezimib, etoposide, quinones including salvicine, and the anthracyclines including doxorubicin, daunorubicin, 4'-epirubicin, idarubicin, and deoxydoxorubicin.

Desirable antiprotozoal agents for combination with DIM-related indoles can also be chosen to be appropriate for out-of-hospital, rural use settings. Such agents are intended for distribution and use as nutraceutical products without prescription or medical supervision. The ingredients need to be safe, stable without refrigeration, and simple to use. Ideally, nutraceutical products will be compatible for use along with other natural product antiprotozoals, especially tea brewed from *Atemesia annua*, the source of artemisinin. Evodiamine, an indole alkaloid component extracted from the fruit of *Evodiae Fuctus* (*Evodia rutaecarpa* Benth.) is an alternative natural product for use with DIM-related indoles. Additional, DIM-related indole compatible herbal medicines and appropriate use is described in the literature (Willcox et al., 2004, BMJ 329(7475): 1156-9).

Dosages and treatment regimens for antimalarial agents are taught in Goodman & Gilman's The Pharmacologic Basis of Therapeutics, Goodman et al. [ed], 9th edition (Jan. 15, 1996) McGraw Hill Text.

4.3.2 Use of DIM-Related Indoles with Antiprotozoal Agents for Malaria 4.3.2.1 Severe Malaria In severe *Plasmodium falciparum* infection with neurological features, termed cerebral malaria (CM), especially impaired consciousness, use of DIM-related indoles is by parenteral route or rectal suppositories. Intravenous DIM-related indole is generally administered in rotation with parenteral quinine or an artemisinin-based drug (e.g., dihydroartemisinin, artemether, or artesunate). The rate of intravenous administration of DIM-related indole and additional anti-malarial agent(s) is based on renal function, hepatic function and overall condition of the patient. This is in addition to parenteral fluids, blood exchange transfusion, osmotic diuretics and correction of hypoglycemia, acidosis and hypovolemia. Oxygen by mask or mechanical ventilation is added to potentiate the anti-parasitic activity of the DIM-related indole and additional anti-protozoal drug. Administration of oxygen therapy is utilized to support the apoptotic mechanisms of action of DIM-related indoles.

4.3.2.2 Moderate-Severe Malaria

Moderately severe malaria is typically characterized by fever and lethargy. When possible, blood tests for parisitemia should be performed to establish the diagnosis and be repeated to document the parasite clearance time (PCT). According to the present invention, treatment is begun with rectal DIM-related indole, preferably in a combined suppository with Artemisinin derivative. Those patients able to take oral fluids simultaneously begin oral DIM-related indole preparation as a suspension or in capsules or tablets. Those subjects with diminished level of consciousness are provided parenteral hydration fluids. When available, oxygen by mask is added to potentiate the anti-parasitic activity of the DIM-related indole and additional anti-protozoal drug. Repeat blood smear examination is performed after 3 days to establish PCT. Oral DIM-related indole therapy is generally given with a second antimalarial drug, preferably an artemisinin or artemisinin derivative, in combination with lumefantrine, mefloquine, sulfadoxine-pyrimethamine, or amodiaquine in chloriquine resistant areas. For use in choloroquine sensitive areas, DIM-related indole therapy is generally given with artimisinin and/or chloroquine. Optimal treatment duration is from 3 to 14 days. A repeat blood smear for parisitemia is again performed at 14 days and again at 28 days.

4.3.2.3 Use with Anti-Malaria Vaccines

Following the administration of a preventive malaria vaccine, typically a sporozoite-based vaccine, oral DIM-related indole therapy is initiated 24-96 hrs following receipt of the vaccine. Optimally, the DIM-related indole composition is given as an oral suspension or tablet in combination with one or more antimalarial drugs selected from artemisinin derivatives, primaquine, atovaquone, proguanil, or pryimentamine-sulfadoxine.

4.3.2.4 Prophylactic Use by Non-Immune Individuals.

In anticipation of exposure to malarial parasites during travel or residence in an endemic area, DIM-related indole therapy is initiated on arrival, continued daily during exposure to risk and further continued 1-2 weeks after the period of exposure. Alternatively, the DIM-related therapy is taken in combination with Chloroquine phosphate (Aralen) 500 mg taken once weekly or in suggested pediatric doses beginning one week prior to exposure and continuing until 2 weeks after exposure in chloroquine sensitive areas. Alternatively, in chloroquine resistant areas, the oral DIM-related indole therapy is taken in conjunction with Atovaqone-proguanin (Malarone) in standard doses, with Mefloquine hydrocholorid (Lariam) in standard doses, with Doxycycline hyclate in standard doses, or with Primaquine phosphate in standard doses. At the option of a supervising physician, the dose of the non-DIM agents can be reduced during the period of prophylaxis when using DIM-related indole therapy. Preferably, the DIM-related indole is combined in the same tablet or capsule with primaquine phosphate. DIM-related indole is combined with an Artemisinin derivative, and optionally additional curcumin for use during pregnancy.

4.3.3 Combined Use of DIM-Related Indoles with Anti-protozoal Agents for Trypanosomiasis In treating advanced African trypanosomiasis during the late menigoencephalitic stage an intravenous suspension or emulsion of DIM-related indole is alternated with intravenous melarsoprol. The combined use is intended to allow a reduction of the melarsoprol dose from the typical 2.0-3.6 mg/kg per day dose of melarsoprol given for 3-4 days once weekly for 3 consecutive weeks. Alternatively, lower doses of melarsoprol from 1-2 mg/kg per day are given with intravenous DIM-related indole for 10 continuous days. For infection due to *T. brucei gambiense*, intravenous or oral DIM-related indole is used in conjunction with intramuscular or intravenous Pentamidine at standard doses for a period of 10 days. For infection due to *T. brucei rhodensiense*, intravenous or oral DIM-related indole is used in conjunction with intravenous Suranim at standard doses for a period of 10 days. Alternatively, in severe cases of African trypanosomiasis, intravenous DIM-related indole is administered in conjunction with intravenous campothecin derivative such as topotectan in standard doses for 10 or more days.

In treating American trypanosomiasis (Chaga's Disease) due to *T. Cruzi*, intravenous or oral DIM-related indole is used in conjunction with intravenous Suranim at standard doses for a period of 10 days for severe disease. Alternatively, oral DIM-related indole is administered in conjunction with oral nifurtimox and/or oral bensnidazole. Alternatively, DIM-related indole is formulated with nifurtimox or bensnidazole in the same flavored oral suspension or pill to improve compliance and ease of use during chronic treatment.

Alternatively, intravenous DIM-related indole is administered in conjunction with intravenous campothectin derivative such as topotectan in standard doses for 10 or more days in severe cases of American trypanosomiasis.

4.3.4 Combined Use of DIM-Related Indoles with Antiprotozoal Agents for Leishmaniasis For the treatment of Leishmaniasis, DIM-related indole therapy is combined with administration of Pentavalent antimony compounds for a more effective therapy. Typically oral or intravenous DIM-related indole is administered in conjunction with sodium stibogluconate given at a dose of 20 mg/kg/day or less for a period of 28 days to treat visceral leishmaniasis. Alternatively, intravenous DIM-related indole is administered in conjunction with intravenous campothectin derivative such as topotectan in standard doses for 10 or more days in severe cases of visceral leishmaniasis. For cutaneous disease the duration of combined treatment is reduced to 20 days. Optionally, a transdermal preparation of DIM-related indoles is added to the orally administered DIM-related indole and applied topically in cutaneous disease. Alternatively, intravenous DIM related indole is administered in combination with liposomal amphotericin B where resistance to antimony-based drugs is identified. When possible, oral therapy for cutaneous disease consists of DIM-related indole given with oral miltefosine. This combination permits a reduction in the standard dose of miltefosine from 100 mg/kg/day. In addition, a DIM-related indole can be administered both orally and topically for use in combination with paromomysin and/or additional gentamicin.

In a alternative preventive approach, a DIM-related indole is administered orally or parenterally with miltefosine and/or a artimesinin derivative in a veterinary formulation formulated as a supplement for dogs or other domestic animals. It can be given in regional programs to reduce transmission from dogs or other domestic animals which serve as a reservoir for the parasite.

4.3.5 Use of DIM-Related Indoles with Antiprotozoal Agents for Protozoal Diarrheal Disease Due to Crytposporidia or Other Coccidial Protozoa DIM related indole therapy for Coccidal diarrhea caused typically by *Cryptosporidium parvum, C. hominis*, or *Cyclospora cayetanensis* is based on symptoms and identification of the protozoal oocytes in stool analysis. In adults, oral DIM-related indoles are typically employed for treatment using a dose range of 50-200 or 50-400 mg twice daily, alone or in conjunction with Nitazoxanide 500 mg twice daily in adults. Children use DIM-related indole as a pediatric suspension providing 25-150 or 25-300 mg twice daily, alone or in conjunction with a suspension of Nitazoxanide providing 200 mg twice daily. Alternatively, capsules containing a combination of DIM, Artemisinin, and curcumin twice daily can be utilized without Nitazoxanide. These capsules are also useful in treating Microsporidial infections caused by *Enterocytozoon* species in immunocompromized patients.

4.3.5.1 Use of DIM-Related Indoles with Antiprotozoal Agents for Toxoplasmosis

Treatment of toxoplasmic encephalitis consists of administration of oral DIM-related indoles using a dose range of 50-200 or 50-300 mg twice daily, alone or in conjunction with pyrimethamine and sulfadiazine along with folinic acid using established protocols in adults. Children use DIM-related indole as a pediatric suspension providing 25-150 or 25-300 mg twice daily, alone or in conjunction with a suspension of pyrimethamine and sulfadiazine along with folinic acid using established pediatric protocols. Alternatively, capsules or pediatric suspensions containing a combination of DIM, Artemisinin, curcumin, and piperine twice daily can be utilized. DIM-related indole at adult doses alone or with Spiramycin can be used during pregnancy.

4.3.6 Combined Use of DIM-Related Indoles with Anti-Protozoal Agents for Trichomonal Disease.

Trichomonal vulvo-vaginitis in women and urethritis in men is treated according to the present invention by administering a DIM-related indole in addition to standard doses of oral metronidazole (Cudmore S L, Delgaty K L, Hayward-McClelland S F, Petrin D P, Garber G E. Treatment of infections caused by metronidazole-resistant *Trichomonas vaginalis*. Clin Microbiol Rev. 2004 October; 17(4):783-93). This can be accomplished by adding DIM, preferably in an absorption-enhanced delivery system (U.S. Pat. No. 6,086,915), and administering 100-200 mg orally once or twice daily for 1-2 weeks. Alternatively, DIM is formulated as a vaginal cream alone or in combination with artesunate for topical administration in infected women. Ideally the vaginal cream is formulated for sustained delivery using site-directed formulation technology to produce unit-dose vaginal creams which are retained on the mucosa. Preferred embodiments utilize formulation techniques described in U.S. Pat. Nos. 6,899,890, 6,214,379, 5,730,997, 5,554,380, 5,445,829, 5,266,329, and US Patent Applications 20030180366 and 20070154516, 20070224226, 20060140990, and 20040062802.

Optionally, the DIM-related indole (50-500 mg) is combined with artemisinin or a derivative such as artesunate, providing 100-300 mg of artesunate per unit dosage. The combination cream is used every 1-3 days in conjunction with oral metronidazole or tinidazole at established doses. Alternatively, the DIM-related indole is combined with Butoconazole (75-200 mg) or Clindamycin (75-200 mg), with optional addition of artemisinin, or artimisinin derivative, to provide a treatment for combined protozoal-bacterial or protozoal-fungal infections. In a further embodiment, the DIM-related indole (50-500 mg) is combined with extracts incorporating the active ingredient from the fruit pericarp of *Sapindus mukorossi* for a topical preparation with both anti-trichomonal and spermicidal activity.

4.3.6.1 Combined Use of DIM-Related Indoles with Anti-Protozoal Agents and Antibiotics for Mixed Vaginal Infections.

DIM related indoles can be formulated in topical emulsions, some with sustained mucosal retention and release of active agents for use in mixed vaginal infection. These uses include DIM related indoles in combination use with clincamycin for bacterial-yeast infections, or alternatively, combined with both clindamycin and artemisinin derivative for bacterial-yeast infections. DIM related indoles can be used with artemisinin derivatives for combined trichomonal-yeast infections, combined with butoconazole for combined trichomonal-yeast infections or alternatively, combined with butoconazole and artemisinin derivatives for combined trichomonal-yeast infections. Preferred embodiments utilize formulation techniques described in U.S. Pat. Nos. 6,899,890, 6,214,379, 5,730,997, 5,554,380, 5,445,829, 5,266,329, and US Patent Applications 20030180366 and 20070154516, 20070224226, 20060140990, and 20040062802. Optionally, DIM related indoles can be used in combination with other useful antiprotozoal agents including metronidazole, or in combination with useful anti-fungal agents, including azole drugs, particularly butoconazole. In addition, natural products drugs or extracts of medicinal plants can be used in combination with DIM related indoles and optional anti-protozoal, anti-bacterial, or anti-fungal agent. Preferred natural products for combined use include evodiamine, curcumin, extracts of Sapindus mukorossi, and sodium butyrate. Additionally, DIM related indoles, and optional additional anti-protozoal agent, can be combined with topically active spermacides for preparations with both microbicidal and contraceptive activities.

4.3.7 Use of DIM-Related Indoles for Intestinal Protozoal Infections in Livestock In certain embodiments of the invention, formulations include combined use of DIM-related indoles with antiprotozoal agents to treat intestinal protozoal infections in livestock due to coccidial or neospora protozoal parasites. In particular, for additives to cattle feed to prevent crytosporidal infection associated abortion during breeding, preferred feed additives utilize, for example, DIM-related indoles, genistein, extracts or derivatives of Artemisia annua, and extracts of Curcuma domestica. Also useful in combination with DIM-related indoles are extracts of Yucca schidigera.

4.3.8 Use of DIM-Related Indoles in Combination with Artemisinin-Based Drugs.

Typically in human use a twice daily oral dose of 50-250 or 50-600 mg/day (1-3 or 1-6 mg/kg/day) of a DIM-related indole in a suitable formulation is taken along with a twice daily oral dose of 25-1000 mg (0.5-10 mg/kg/day) of dihydroartemisinin, artesunate or other artemisinin-derived drug in a suitable formulation.

In a preferred embodiment, a twice daily oral dose of 50-550 mg/day (1-3 mg/kg/day) of DIM-related indole in a suitable formulation is taken along with a twice daily oral dose of 25-1000 mg (0.5-10 mg/kg/day) of dihydroartemisinin, artesunate, or other artemisinin-derived drug in a suitable formulation, together with curcumin at a twice daily oral dose of 25-1000 mg (0.5-10 mg/kg/day) and piperine to aid absorption. Typically 20-150 mg of DIM related indole is combined with 25-1500 mg (0.5-10 mg/kg/day) Artemesinin extract and 25-1500 mg (0.5-10 mg/kg/day) of curcumin and 20 mg of piperine 20 mg. Preferably the extract of piperine is called Bioperine® (an extract from the fruit of Piper nigrum L (black pepper) or Piper longum L (long pepper) containing 95 percent piperine; Sabinsa Corporation, Piscataway, N.J.). The DIM-related indole, artemisinin-related drug, curcumin and piperine are preferably contained in the same capsule or tablet to facilitate combined use.

In a second preferred embodiment, the DIM-related indole and artemisinin derivative (preferably artesunate) is formulated using site-directed formulation technology to produce unit-dose vaginal or rectal suppositories/creams which are retained on the mucosa for sustained delivery. Related, optional embodiments utilizes formulation techniques described in U.S. Pat. Nos. 6,899,890, 6,214,379, 5,730,997, 5,554,380, 5,445,829, 5,266,329, and US Patent Applications 20030180366 and 20070154516, 20070224226, 20060140990, 20040062802, and 20020044961.

For severe protozoal disease as seen with cerebral malaria, African sleeping sickness, acute Chaga's disease, and visceral Leismaniasis, the DIM-related indole is preferably give intravenously. DIM is given in a suitable intravenous suspension or emulsion to deliver 2-15 mg/kg per dose every 8 to 12 hours. DIM may be administered with quinine in malaria, with eflornithine, pentamidine, melarsoprol, nifurtimox, or benznidazole, for tryanosomiasis, and with pentavalent antimony, amphotericin B, or miltefosine in Leishmaniasis.

For life threatening conditions, intravenous DIM-related indoles would be administered with or without DIM suppositories and/or additional aerosolized DIM. Oxygen therapy is added to potentiate parasite clearance using DIM-related indoles.

4.4 Administration and Dosage

In certain embodiments, certain combinations of DIM-related indoles, e.g., DIM, and one or more known antiprotozal agents in parenteral delivery systems, oral delivery systems, rectal suppositories, vaginal creams, or by simultaneous delivery by multiple routes provides therapeutic efficacy are believed to provide more than the additive efficacy of each agent used alone at maximal dose. Therefore, methods involving combined use of a DIM-related indole and a known antiprotazal agent at less than their maximal doses increase both the safety and efficacy of DIM-related indoles and antiprotazal agents in selected protozoal infections.

Improved efficacy results in a shorter duration of required therapy than with individual agents used alone. Combined use can allow a reduction in dose or shortening of the period of high dose treatment. Combined use can improve the long term therapeutic result with a lower rate of recrudescence with renewed appearance and growth of surviving parasites. Combined use with lowered dose and duration of use can minimize toxicity.

In methods involving the oral use of one or more DIM-related indoles, e.g., DIM, and one or more known antiprotozal agents, the oral delivery of indole is facilitated and accomplished according to formulations and methods described in U.S. Pat. No. 6,086,915, incorporated by reference herein in its entirety. In one embodiment, DIM, or a DIM-related indole, is processed with phosphatidyl choline. Alternatively, oral and rectal bioavailability of DIM-related indoles are improved using other means including particle size reduction, complexation with phosphatidylcholine, and formation into rapidly dissolving particles and nanoparticles.

The treatment of protozoal disease with an oral DIM-related indole, e.g., DIM, is facilitated by oral, sublingual, intravenous, rectal, vaginal, transdermal, and intra-lesional application of DIM-related indoles in specific relative doses with simultaneous administration of a known antiprotazoal agent. These therapies include production of tinctures, liposomes, creams, or rectal/vaginal suppositories, emulsions for intravenous use, and injectable suspensions to deliver synergistic amounts of these agents. Injectable formulations include cyclodextrin complexed DIM-related indoles and liposome encapsulated DIM-related indoles.

For oral use, DIM is used, preferably formulated for enhanced absorption in a daily dose of 0.5-12 mg/kg per day. Oral DIM is optionally combined with other oral agents for malaria, trypanosomiasis, leishmaniasis, crytosporidiosis, and toxoplasmosis using standard doses of the additional agents.

For intravenous use, DIM is used, preferably formulated as an intravenous suspension or emulsion, in a daily dose of 0.5-15 mg/kg per day. Intravenous DIM is optionally combined with other intravenous and oral agents for malaria, trypanosomiasis, leishmaniasis, crytosporidiosis, and toxoplasmosis using standard doses of the additional agents.

For rectal use, DIM is preferably formulated for enhanced rectal absorption in suppositories in a daily dose of 0.5-12 mg/kg per day. DIM is optionally combined with other rectal agents for malaria (artesunate, artemether), trypanosomiasis (eflornithine, nifurtimox), leishmaniasis (miltefosine), crytosporidiosis (artesunate, artemether), and toxoplasmosis (pyrimethamine and sulfadiazinwe) using standard doses of the additional agents.

For vaginal or rectal use the DIM-related indole is formulated using site-directed formulation technology to produce unit-dose vaginal or rectal suppositories/creams which are retained on the mucosa for sustained delivery. Preferred embodiments utilize formulation techniques described in U.S. Pat. Nos. 6,899,890, 6,214,379, 5,730,997, 5,554,380, 5,445,829, 5,266,329, and US Patent Applications 20030180366 and 20070154516, 20070224226, 20060140990, 20040062802, and 20020044961. Optionally, the DIM-related indole is combined with artemisinin derivative (e.g., artesunate), butoconazole, tinidazole, niridazole, nitazoxanide, or miltefosine, 4.5 Pharmaceutical/Nutraceutical Compositions Pharmaceutica/Nutraceutical Dosage Forms for DIM-related indoles: Multi-application DIM-related indole containing particles are manufactured by various techniques including spray drying, spray cooling, selective precipitation, crystallization and other particle forming methods. The resulting particles are used in the manufacture of the following dosage forms, some of which are described in U.S. Pat. No. 6,086,915, incorporated by reference herein in its entirety.

I. Spray Dried Microencapsulated Solid Dispersions
1. TPGS/phosphospholipid spray-dried particles. Production of absorption-enhanced DIM-related indole particle formation is provided in U.S. Pat. No. 6,086,915.
2. Liquid emulsions using TPGS/phosphospholipid spray-dried particles. Production of emulsions for oral use utilizes absorption-enhanced DIM-related indole particle formation is provided in the U.S. Pat. No. 6,086,915.
3. Flavored DIM granules for oral use (Chocolate, Orange "sprinkles"). Production of flavored granules for oral use utilizes absorption-enhanced DIM-related indole particles (DIM/TPGS) as provided in U.S. Pat. No. 6,086,915. Production steps include dry mixing DIM/TPGS particles with maltodextrin granules, addition of flavoring particles and granulation using a standard fluid bed granulator.

II. Spray Dried Polymer Based Solid Dispersions

Production techniques for DIM-related indoles may utilize those described in U.S. Patent Application No. 20030072801, entitled "Pharmaceutical compositions comprising drug and concentration-enhancing polymers," herein incorporated by reference in its entirety. In particular production involves the following dissolution enhancing polymers, used with and without lipid stabilizers:
1. Polymer included: Hydroxy Propyl Methylcellulose
2. Polymer: Hydroxy Propyl Cellulose III. Cyclodextrin Based Formulations Examples of manufacturing techniques are described in U.S. Pat. No. 4,877,778 and U.S. Patent Applications Nos. 20040053888; 20030073665; and 20020068720, each of which is herein incorporated by reference in its entirety. Using cyclodextrin loading production techniques to incorporate DIM-related indoles the following final formulations are produced:
1. Dry particle complex for oral use
2. Intravenous emulsion
3. Parenteral emulsion IV. Nanoparticle-Based Dispersions Examples of manufacturing techniques are described in U.S. Pat. Nos. 6,288,040; 6,165,988; 6,117,454; and U.S. Patent Application Publication No. 20030032601; each of which is incorporated by reference in its entirety. Using nanoparticle production techniques to incorporate DIM-related indoles the following final formulations are produced:
1. Dry particle complex for oral use.
2. Intravenous emulsion
3. Parenteral emulsion V. Liposome Based Formulations Examples of manufacturing techniques are described in U.S. Pat. Nos. 4,906,476; 5,006,343; and U.S. Patent Application Publication No. 20030108597. Using liposome production techniques to incorporate DIM-related indoles the following final formulations are produced:
1. Dry particle complex for oral use
2. Intravenous emulsion
3. Parenteral emulsion 4.5.1 Oral Combined Products Combined formulations for oral use include DIM-related indole, optionally formulated for enhanced absorption, combined with one or more additional anti-protozoal compounds and optionally include additional absorption enhancers. Examples of preferred antiprotozoal compounds include artemisinin; dihydroartemisinin; artemethe; artesunate; atovaqone; diaminopyrimidines, especially amodiaquine, amphotericin, clindamycin, eflornithine, fumagillin; the 8-hydroxyquinolines, choroquine, mefloquine, halfantrine, lumefantrine, geldanamycin, iodoquinol (diiodohydroxyquin) and clioquinol (iodochlorhydroxyquin); the 2-nitroimidazoles including Etanidazole and Benznidazole; doxycycline; melarsoprol; metronidazole; miltefosine; nifurtimox; nitazoxanide; paromomycin; pentamindine; sodium stibogluconate and related antimonials; suramin; pyrimethamine; proguanil (chloroguanide); spiramycin; sulfadoxine; sulfonomides including trimethoprim; sulfones; and tetracyclines; quinine derived from the bark of the South American chinchona tree; 6-gingerol and/or 6-paradol (Surh et al., 1999, J Environ Pathol Toxicol Oncol. 18(2):131-9); and selected flavonoids and derivatives (Tasdemir et al., 2006, Antimicrob Agents Chemother. 50(4):1352-64). Other antiprotozoal compounds include, but are not limited to, curcumin, an extract of *Curcuma domestica*, leutiolin, selenium compounds, especially methylselenic acid, resveratrol, including an extract of *Polygonium cuspidatum*, silibinin, an extract of *Silybunz marianum*, apigenin, deguelin, extracted from various plant sources including *Munduelea sericea*, Evodiamine, ursolic acid, Andrographolide, Dehydro-Andrographolide, Deoxy-Andrographolide, Brassinin, Caffeic acid, Capsanthin, Capsaincin, Chelerythrine Chloride, Cromolyn sodium, Allyl Disulfide, Diallyl disulfide, Diallyl sulfide, Diallyl trisulfide, Dibenzoylmethane, Ebulin 1, Ellagic acid, Ferulic acid, 18β-Glycyrrhetinic Acid, Glycyrrhizic acid ammonium salt trihydrate, Honokiol, 5-Hydroxy-L-tryptophan, Hypericin, Hypocrellin A, Idebenone, luteolin, D-Limonene, Limonin, Limonin Glucoside, DL-α-Lipoic acid, Melatonin, Perillyl Alcohol, Phenylbutyrate, Phenylethyl 3-methylcaffeate, Phenylethy 14-methylcaffeate, Phenyl isothiocyanate, Phytic Acid, Rosmarinic acid, Rutaecarpine, sulforaphane, L-Threonine, Trichostatin A, aspirin, salycylamide. Absorption-enhancing agents can be additionally added including, but not limited to, Vitamin-E polyethyleneglycol succinate (TPGS), piperine, limonine, D-Limonene, and/or polyethyleneglycol. In addition, orally active immune potentiating agents can be utilized in addition to anti-protozoal agents including Vitamin K3, N-Acetyl-L-Cysteine, Zinc citrate, or Zinc gluconate.

The DIM, or a DIM-related indole, together with one or more antiprotozoal compounds and optionally, an antiprotozoal plant extract can also be added to selected foods as fortified, "functional" foods. Fortified foods include "medicinal foods" which require use under a doctor's care and "functional foods" available to consumers as unregulated specialized foods. Such uses in fortified or "functional" foods typically apply to Food Bars, Drink Mixes, Vegetable Juices, Pasta Mixes, Dry Cereal, Meal Replacement Powders, Tea mixes, and Baked Goods. Such uses require specialized production with the dose of DIM in accordance with principles of Generally Regarded As Safe (GRAS) food ingredients. These typically include drink mixes, meal replacement powders, food bars, and candies. Formulations include DIM, or a DIM-related indole, and one or more of the following antiprotozoal compounds: artemisinin, genistein, curcumin, and resveratrol. The compositions of DIM, and DIM-related indoles, of the present invention are also utilized as added ingredients to fortified foods to facilitate convenient and regular consumption to prevent or control chronic protozoal parasite infection. Antiprotozoal fortified foods with DIM are used in periodic "cleansing" programs, where special diets and intermittent fasting is use to reduce intestinal parasite infection. In such applications DIM is added to food products or mixes alone or in combination with selected antiprotozoal compounds, particularly artemisinin, curcumin, and isoflavones like genistein.

Food Bar Products are produced according to the present invention according to known manufacturing and baking practices. Detailed of food bar composition and manufacturing techniques useful with DIM, DIM-Related Indoles, and DIM combined with selected antiprotozoal compounds are specified in U.S. Patent Application Publication Nos. 20030068419 entitled "Food bar compositions" and 20020168448 entitled "Nutritional food bar for sustained energy".

Drink Mix Products are produced according to the present invention according to known manufacturing practices. Detailed drink mix composition and manufacturing techniques useful with DIM, DIM-Related Indoles, and DIM combined with selected antiprotozoal compounds are specified in U.S. Pat. No. 6,599,553 by Kealey et al., entitled "Dry drink mix and chocolate flavored drink made therefrom".

In preferred embodiments, DIM is incorporated in fortified foods, such as drink mixes and food bars, during food production using a particulate form of DIM that is formulated for enhanced absorption (BioResponse-DIM [BioResponse, LLC, Boulder, Colo.]). Artemisin is added as a powdered extract of *Artemisia annua*(Artemisin [Allergy Research Group, Alameda, Calif.]). Genistein is added as a powdered formulation of pure isoflavone (Bonistein [DSM Nutritional Products]). Typically, the DIM is provided in a dose of 10-75 mg/serving (40-300 mg/serving of BioResponse-DIM). Artemisinin is provided in a dose of 50-300 mg/serving. Genistein is provided in a dose of 25-100 mg/serving as Bonistein.

4.5.2 Mucosally Targeted Formulations

Mucosally targeted formulations includes specialized emulsions of DIM-related indoles, optionally combined with known anti-protozoal agents which are retained on and penetrate the targeted mucosa for long periods of time. This includes specialized formulations for oral, esophageal, rectal, vaginal, and vulvar mucosa. This formulation technology provides a preferred way of treating Trichomonal infection, Candidal infection, and Crytosporidial infection. For vaginal or rectal use the DIM-related indole is formulated using site-directed formulation technology to produce unit-dose vaginal or rectal suppositories/creams which are retained on the mucosa for sustained delivery. One related embodiment utilizes formulation techniques described in U.S. Pat. Nos. 6,899,890, 5,554,380, 5,266,329, and US Patent Applications 20030180366 and 20070154516. Optionally, the DIM-related indole is combined with artemisinin derivative (eg, artesunate), butoconazole, clindamycin, tinidazole, niridazole, nitazoxanide, or miltefosine, 4.5.3 Hepatic Targeted Formulations Hepatic targeting includes intravenous emulsions which are concentrated in liver tissue with or without lipids and, optionally including anti-protozoa-specific antibodies. Concentration in hepatic tissue provides an advantage in treating the hepatic stage of malaria.

1. Phospholipid complexed intravenous emulsions
2. Cyclodextrin-based intravenous emulsions
3. Intravenous suspension complexed with Anti-protozoal monoclonal antibodies 4.5.4 Leukocyte Targeted Formulations Leukocyte targeting includes intravenous emulsions which are concentrated in leukocytes with or without lipids and Anti-protozoa-specific antibodies. Concentration in leukocytes provides an advantage in treating the leukocyte stage of trypanosomal and leishmanial infections.

1. Phospholipid complexed intravenous emulsions
2. Cyclodextrin-based intravenous emulsions
3. Intravenous suspension complexed with Anti-Protozoal monoclonal antibodies 4.5.5 DIM Tinctures and Suspensions Tincture preparation allows a simple absorbable liquid formulation of DIM-related indole to be prepared for use in a rural setting. A mixture of DIM-related indole is manufactured with optional, additional anti-protozoal compound using ethanol as a solvent to provide various tincture formulations. Methods for making tinctures appropriate for anti-protozoal compounds are described by Sweet in U.S. Pat. No. 7,033,619, entitled "Method for making herbal extracts using percolation" and methods specific for Atemesinin tinctures described in U.S. Pat. No. 4,952,603.

1. Oral tinctures prepared with ethanol or hexanol
2. Parenteral tincture prepared with ethanol or hexanol
3. Microcrystalline suspension for oral use
4. Parenteral microcrystalline suspension
5. Sustained release parenteral suspension Pharmaceutical compositions according to the present invention preferably comprise one or more pharmaceutically acceptable carriers and the active constituents, e.g., a DIM-related indole alone, or a DIM-related indole and one or more known antiprotozal agents. The carrier(s) must be "acceptable" in the sense of being compatible with the other ingredients of the composition and not deleterious to the recipient thereof.

The term "carrier" refers to a diluent, adjuvant, excipient, or vehicle with which the therapeutic is administered. The carriers in the pharmaceutical composition may comprise a binder, such as microcrystalline cellulose, polyvinylpyrrolidone (polyvidone or povidone), gum tragacanth, gelatin, starch, lactose or lactose monohydrate; a disintegrating agent, such as alginic acid, maize starch and the like; a lubricant or surfactant, such as magnesium stearate, or sodium lauryl sulphate; a glidant, such as colloidal silicon dioxide; a sweetening agent, such as sucrose or saccharin; and/or a flavoring agent, such as peppermint, methyl salicylate, or orange flavoring.

It will be appreciated that the amounts of DIM or other DIM-related indole and/or one or more known antiprotozal agents, required for the treatments disclosed herein will vary according to the route of administration, the severity of the protozoal disease, age, and medical history of the subject, the galenic formulation of the pharmaceutical composition, etc.

Preferably, the DIM used in the invention has been processed to enhance bioavailability, as is described in U.S. Pat. No. 6,086,915, incorporated herein by reference in its entirety; however any suitable preparation of pure diindolylmethane can be used in the methods and compositions of the invention. Optionally, additional absorption enhancing agents active with DIM-related indole such as grapefruit extracts or extract of black pepper providing extracts of piperine can be included.

In general, a suitable (therapeutically effective) amount of Diindolylmethane is preferably administered in an absorption enhancing formulation, as described in U.S. Pat. No. 6,086,915, at 25-750 mg per day as a suspension of microparticles in a starch carrier matrix. Structurally-related, synthetically-derived, substituted diindolylmethane's, as described by Jong (U.S. Patent Application Publication No. 2004/0043965) are administered according to the present invention in an acceptable formulation for oral administration in a dose of 10-400 mg/day. Preferably, these substituted diindolylmethanes are administered in an absorption-enhanced formulation at a dose of 50 to 250 mg/day. The actually administered amounts of DIM or a substituted diindolylmethane may be decided by a supervising physician. The DIM-related indole of the invention is preferably administered in combination with one or more known antiprotozal agents administered by either oral, rectal, or parenteral routes.

Therapeutic formulations include those suitable for parenteral (including intramuscular and intravenous), topical, oral, vaginal, rectal or intradermal administration. Thus, the pharmaceutical composition may be formulated as tablets, pills, syrups, capsules, suppositories, ophthalmic suspension, formulations for transdermal application, powders, especially lyophilized powders for reconstitution with a carrier for intravenous administration, etc. Oral administration for DIM is the most preferred route.

Therapeutic formulations suitable for oral administration, e.g., tablets and pills, may be obtained by compression or molding, optionally with one or more accessory ingredients. Compressed tablets may be prepared by mixing phytochemicals, and compressing this mixture in a suitable apparatus into tablets having a suitable size. Prior to the mixing, the DIM-related indole or one or more antiprotozoal agents may be mixed with a binder, a lubricant, absorption enhancer, an inert diluent and/or a disintegrating agent.

In a preferred embodiment, the DIM-related indole is mixed with a binder, such as microcrystalline cellulose, and a surfactant, such as sodium lauryl sulphate until a homogeneous mixture is obtained. Subsequently, another binder, such as polyvinylpyrrolidone (polyvidone), is transferred to the mixture under stirring with a small amount of added water. This mixture is passed through granulating sieves and dried by desiccation before compression into tablets in a standard tableting apparatus.

A tablet may be coated or uncoated. An uncoated tablet may be scored. A coated tablet may be coated with sugar, shellac, film or other enteric coating agents.

Therapeutic formulations suitable for parenteral administration include sterile solutions or suspensions of the active constituents. An aqueous or oily carrier may be used. Such pharmaceutical carriers can be sterile liquids, such as water and oils, including those of petroleum, animal, vegetable or synthetic origin, such as peanut oil, soybean oil, mineral oil, sesame oil and the like. Formulations for parenteral administration also include a lyophilized powder comprising phytochemical that is to be reconstituted by dissolving in a pharmaceutically acceptable carrier that dissolves said phytochemical. Parenteral administration also includes a stable emulsion of DIM designed for intravenous use. Ideally, the emulsion prevents the early removal of DIM from the circulation due to early uptake by the reticulo-endothelial system allowing maximal cellular concentration of DIM in parasite-infected cells or tissue.

When the pharmaceutical composition is a capsule, it may contain a liquid carrier, such as a fatty oil, e.g., cacao butter.

Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. These compositions can take the form of solutions, suspensions, emulsion, tablets, pills, capsules, powders, sustained-release formulations and the like. The composition can be formulated as a suppository, with traditional binders and carriers such as triglycerides or nerolidol, a sesquiterpene.

In yet another embodiment, the therapeutic compound can be delivered in a controlled release system. In one embodiment, a pump may be used (see Langer, supra; Sefton, CRC Crit. Ref. Biomed. Eng. 1987, 14:201; Buchwald et al., Surgery 1980, 88:507; Saudek et al., N. Engl. J. Med. 1989, 321:574). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J. Macromol. Sci. Rev. Macromol. Chem. 1983, 23:61; see also Levy et al., Science 1985, 228:190; During et al., Ann. Neurol. 1989, 25:351; Howard et al., J. Neurosurg. 1989, 71:105).

Other controlled release systems are discussed in the review by Langer (1990, Science 249:1527-1533).

In one embodiment of the pharmaceutical composition according to the invention, the DIM-related indole and one or more known antiprotozal agents are comprised as separate entities. The entities may be administered simultaneously or sequentially.

The invention also provides a pack or kit comprising one or more containers filled with one or more of the ingredients of the compositions of the invention. This includes the combination of capsules for oral use and rectal suppositories. Optionally associated with such container(s) can be a notice in the form prescribed by a governmental agency regulating the manufacture, use or sale of pharmaceuticals or biological products, which notice reflects approval by the agency of manufacture, use or sale for human administration.

A number of references have been cited, the entire disclosures of which are incorporated herein by reference.

Many modifications and variations of this invention can be made without departing from its spirit and scope, as will be apparent to those skilled in the art. The specific embodiments described herein are offered by way of example only, and the invention is to be limited only by the terms of the appended claims along with the full scope of equivalents to which such claims are entitled.

5. EXAMPLES

5.1 Example 1

Manufacture of Processed DIM for Enhanced Oral Bioavailability

Preparation of processed Diindolylmethane is accomplished according to the steps outlined in U.S. Pat. No. 6,086, 915, herein incorporated by reference in its entirety. Briefly, this included mixture of about 10-40% by final weight of Diindolylmethane with about 10-40% by final weight of vitamin E polyethylene glycol 1000 succinate (Vitamin-E-TPGS, Eastman Chemical), 2-20% by final weight, phosphatidyl choline (Phospholipon 50G, Rhone Poulenc) and 15-30% by final weight hexanol. This mixture is made homogeneous by mixing. The homogeneous mixture of indoles and other oil soluble substituents listed above is added to a solution of modified starch in water (Capsul Starch from National Starch, Inc.). The starch component forms from 30-70% of the final dry weight of the product. The well dispersed final combined mixture is then subjected to spray drying. The resultant product is a fine powder containing Diindolylmethane contained within the starch particles.

5.2 Example 2

Manufacture of Capsules Containing Diindolylmethane and Optional Antiprotozoal Agent(s)

Capsules containing 150-300 mg of processed Diindolylmethane, as produced according to the steps described in example 6.1, are made by mixing the processed Diindolylmethane with microcrystalline cellulose and placing the mixed powder into opaque gelatin capsules.

Capsules containing the combination of about 150 mg of processed DIM (providing 50 mg of DIM) and 200-500 mg of Artemisinin, and/or other Artemisinin derivatives are made by mixing the processed DIM, and Artemisinin with microcrystalline cellulose or rice flour excipient and placing the mixed powder into opaque gelatin capsules. Alternatively, capsules or tablets with about 150 mg of processed DIM providing 50 mg of DIM and 200-500 mg of Artemisinin, or other Artemisinin derivatives, Curcumin 100-200 mg, and piperine 20 mg are made with microcrystalline cellulose or rice flour excipient and by placing the mixed powder into opaque gelatin capsules.

5.3 Example 3

Manufacture of Flavored, Pediatric Suspensions of DIM-Related Indoles

DIM-related indoles are incorporated into pediatric suspensions manufacture as powdered mixtures to be re-constituted with water prior to use in patients. The suspension products have the advantages of long shelf life, stability and flavoring for taste masking to improve palatability.

A DIM-related indole containing suspension is made using established manufacturing techniques as described in U.S. Pat. No. 6,586,012 by Yu et al. issued Jul. 1, 2003, and titled, "Taste masked pharmaceutical liquid formulations". When reconstituted, the pediatric suspension has a DIM related indole concentration of 15-30 mg/ml of suspension. Typically, 3-10 mg/kg/dose of DIM related indole is administered twice daily. Alternatively, DIM-related indole pediatric suspensions are manufactured using techniques described by Kulkarni et al. in U.S. Patent application No. 20050136114, published Jun. 23, 200, and titled, "Taste masked pharmaceutical compositions comprising bitter drug and pH sensitive polymer".

In a preferred embodiment the DIM-related indole is formulated into a pediatric suspension in combination with an artemisinin derivative, such as artesunate, curcumin and piperine utilizing taste masking.

5.4 Example 4

Manufacture of DIM with Artemisinin Derivative in a Suppository for Vaginal or Rectal Administration In a heated vessel, 90 grams cetostearyl alcohol (Alfol 16/18, Vista) mixed with 10 cc Grapefruit Oil (Aldrich Chemical) was heated to 100° C. to which 20 gms of microcrystalline DIM, 5 or 10 gms of Artesunate (LKT Labs, St. Paul, Minn.), were added with constant mixing to form a hot slurry. Alternatively, 90 grams cetostearyl alcohol (Alfol 16/18, Vista) is heated to 100° C. to which 10 gms of microcrystalline DIM is mixed and to which is added in a second vessel 400 gms of IV Novata (Semi-synthetic Glyceride Suppository Base, Ashland Chemicals) was warmed to 40° C. with constant mixing. The well mixed slurry from the first vessel was added with continued mixing to the second vessel. The homogenized molted suppository material was formed into suppositories of 2 g each and cooled. Glyceryl monosterate 10-50 g was added to the molten mixture as needed to increase the firmness of the final suppositories. Optionally, 50-100 mg of artesunate or arthemether is added per suppository for children, and 200-300 mg of artesunate or artemether is added per suppository for adults.

Other methods of producing suppositories are well know in the art as described in U.S. Pat. No. 4,164,573 by Galinsky et al., issued Aug. 14, 1979 and titled, "Composition and method for making a suppository for introducing a hypoglycemic agent into a mammal". Use of this method provides a technique to manufacture a mixture of DIM and Artemisinin-related compound which is then evaporated into a semisolid mass and then shaped into suppository. In a preferred product format the suppository would contain 50-100 mg of DIM and 50-100 mg of artesunate for children, and 100-300 mg of DIM and 200-300 mg of artesunate for adults. Optionally, Vitamin E TPGS (Eastman Chemical) or nerolidol, a sesquiterpene, are added to suppository formulations as drug penetration enhancers.

5.5 Example 5

Manufacture of Sustained-Release Combination Formulas for Vaginal or Rectal Administration Mucosally targeted formulations includes specialized emulsions of DIM-related indoles, optionally combined with known anti-protozoal agents which are retained on and penetrate the targeted mucosa for long periods of time. This includes specialized formulations for oral, esophageal, rectal, vaginal, and vulvar mucosa. This formulation technology provides a preferred way of treating Trichomonal infection, Candidal infection, and Crytosporidial infection. For vaginal or rectal use the DIM-related indole is formulated using site-directed formulation technology to produce unit-dose vaginal or rectal suppositories/creams which are retained on the mucosa for sustained delivery. One related embodiment utilizes formulation techniques described in U.S. Pat. Nos. 6,899,890, 5,554,380, 5,266,329, and US Patent Applications 20030180366 and 20070154516. Optionally, the DIM-related indole is combined with artemisinin derivative (eg, artesunate), butoconazole, clindamycin, tinidazole, niridazole, nitazoxanide, or miltefosine,

5.6 Example 6

Manufacture of Cyclodextrin Complex Formulations with DIM-Related Indoles for Improved Bio-Delivery Introduction: As poorly soluble drug agents, DIM-related indoles, in general, require solubility enhancing formulation steps which are bio-compatible for parenteral and improved oral drug delivery. Parenteral formulations for intramuscular, intravenous, and pulmonary aerosol delivery benefit from complexation with various cyclodextrins (alpha-cyclodextrin, beta-cyclodextrin, hydroxypropyl-beta-cyclodextrin, and sulfobutylether-beta-cyclodextrin).

Methods: Specific formulations and formulation steps are developed utilizing cyclodextrins. Formulations are based on methods and observations that molecules containing indole rings successfully complex with cyclodextrins providing a subsequent solubility advantage over the indole alone (Cao et al., 2000, Chemosphere 40:1411-6). Therefore, prototype formulation utilizing microcrystalline DIM, compatible solvent systems, with and without lipid stabilizers are manufactured using spray drying technology. Dry particle products are appropriate for suspension in aqueous vehicles for intramuscular or intravenous drug delivery.

Preferred cyclodextrins utilized are:

1. β-cyclodextrin, which is generally more applicable for the complexation of hydrophobic molecules. It is anticipated that 2 molecules of β-cyclodextrin will be needed per molecule of DIM.
2. Hydroxypropyl β-cyclodextrin, which is known to be very soluble, on the order of 30% and more.
3. Sulfobutyl β-cyclodextrin (trade-name Captisol®). Captisol has a molecular weight of ~2200 mg/mmol so at 2:1 cyclodextrin to DIM, the amount of DIM that can be put into solution will be considerably higher than the known solubility of DIM.

Sample preparations to be undertaken:

Pharmaceutically acceptable solvents will be utilized to form solutions for spray drying with Hydroxypropyl β-cyclodextrin and Sulfobutyl β-cyclodextrin. Complexes of each of the β-cyclodextrins with DIM will be prepared with a slight excess of the cyclodextrin and spray dried to produce approximately 10 to 20 grams of each formulation. Further formulation suitable for intravenous, intramuscular and pulmonary aerosol use will utilize published manufacturing techniques (Steckel et al., 2004, Int J Pharm. 278:187-95).

Testing of Prepared DIM-Cyclodextrin Formulations:

Prepared samples will be analyzed as to amorphous crystal structure and stability using standard techniques (Rodriguez-Spong et al., 2004, Adv Drug Deliv Rev. 56:241-74). Testing of prepared formulations will include release testing of DIM in simulated gastric acid. In vivo release and bioavailability testing in animal and human models will utilize plasma DIM assays as described in U.S. Patent Application Publication No. 20030096855.

Conclusions: Cyclodextrin DIM Spray-dried formulations are expected to demonstrate shelf stability, form stable suspensions in 5% dextrose solutions for intravenous administration, and stable suspensions in 0.9% NaCl for intramuscular, parenteral administration.

5.7 Example 7

Sterile Intravenous Microemulsions of DIM for Use in Conjunction with Protozoal Parasite Treatment Stable microemulsions of DIM, designed for intravenous use, are developed to provide a convenient means of administering DIM to achieve high tissue concentrations of DIM quickly and at a predictable time. This use facilitates the use of DIM in anti-protozoal therapy. In addition, microemulsions of DIM can be used in conjunction with other anti-protozoal agents. In alternative embodiments, DIM analogues including imidazolelyl-3,3'-diindolylmethane, including nitro substituted imidazolelyl-3,3'-diindolylmethanes and DIM derivative SR13668 (Stanford Research Institute) can be used in protozoal parasite infections.

The low solubility of DIM in both water and lipid requires development of a specialized micro-emulsion that utilizes phospholipids to optimize the solubility of DIM and improve the stability of the microemulsion. To prepare the microemulsion Ethyl oleate (EO), Phosphatidyl Choline (PC) (from egg yolk), and calcein, are purchased from Sigma-Aldrich, Inc (St. Louis, Mo.). Distearoyl-phosphatidylethanolamin-N-poly(ethyleneglycol) 2000 (DSPE-PEG) is purchased from Avanti Polar Lipids (Alabaster, Ala.).

Using a modification of the method of Yu et al. (Yu et al., 1993, Int. J. Pharm. 89:139-146), the microemulsion is manufactured as follows: 160 grams of EO and 60 grams of PC are dissolved in 1 liter pure ethanol. 24 grams of microcrystalline DIM (mean particle size 0.25 micron) is added and dissolved in this "oily phase". 20 grams of DSPEG-PEG is then dissolved in 500 cc of USP water (Aqueous phase). The oily ethanolic solution (oily phase) with the dissolved DIM is then slowly added into the DSPE-PEG solution (aqueous phase) under moderate magnetic stirring. The aqueous phase immediately turns milky with opalescence as the result of the microemulsion produced. The microemulsion is then subjected to low pressure at 360 mm Hg and maintained at 50° C. The low pressure is used to concentrate the emulsion through removal of the ethanol and a portion of the water. Using an infrared absorption assay to determine the DIM content of the microemulsion, a final concentration of DIM of 7.5 mg/ml is established. Sodium hydroxide is added to increase the pH to the 5.0-7.5 range.

Using this manufacturing technique emulsions of DIM are prepared and subjected to stability testing to demonstrate that the particle size within the emulsion remained between 150 and 200 nm. The production technique results in a microemulsion with % weight ranges of the components in the following preferred ranges:

| Component | Approx % Weight |
|---|---|
| DIM | 0.05-0.1 |
| Lipids (EO:PC:DSPE-PEG; 8:3:1) | 45-28 |
| Water | 50-70 |
| Ethanol | 1-2 |

Alternatively, an ethanol-free production method can be utilized to produce a stable micro-emulsion of DIM or DIM derivatives and analogues, using Lipofundin MCT B (Braun Melsungen AG, Melsungen, Germany), a preformed basic emulsion, and high pressure homogenization of microcrystalline DIM. This method utilizes jet-milled DIM, with particle size reduced to 0.1 micron average diameter (performed by Micron Technologies, Inc., Exton, Pa.). Using this technique 700 mg of 0.1 micron diameter DIM crystals are homogenized in 100 cc Lipofundin using equipment and methods as described (Akkar et al., 2003, Eur J Pharm Biopharm. 55:305-12). This results in a stable lipid-based microemulsion with particle size less than 200 nm and a DIM content of 7 mg/cc of the emulsion.

5.8 Example 8

Sterile Liposome-Encapsulated DIM for Oral, Rectal, and/or Intravenous for Use in Conjunction with Antiprotozoal Therapy Liposomes are microscopic vesicles composed of a phospholipid bilayer that encapsulate active agents for specialized delivery to specific tissues. In certain embodiments, liposome encapsulated DIM formulations are developed to provide increased concentration of DIM in hepatic and pulmonary tissue in anti-protozoal therapy. Manufacturing techniques for DIM Liposomes are developed based on the published liposome manufacturing techniques as described in U.S. Pat. Nos. 4,906,476; 5,006,343; and U.S. Patent Application Publication No. 20030108597, each of which is incorporated by reference herein in its entirety. The preferred techniques for producing DIM liposomes are those that result in liposomes which accumulate in lung and respiratory epithelial tissue.

Liposomes are formulated utilizing N-(carbonyl-methoxy-polyethylene glycol 2000)-1,2disteaoyl-sn-glycero-3-phosphoethanolamine sodium salt (MPGEG-DSPE) (2-4 mg/ml); fully hydrogenated soy phosphatidylcholine (HSPC) (2-11 mg/ml); and cholesterol (1-4 mg/ml). Each 30 ml vial produced contains 30-60 mg of DIM-related indole at a concentration of 1-2 mg/ml.

DIM Liposomes can be utilized in hospitalized cases of protozoal disease every 8 to 12 hours. DIM Liposomes are preferably administered intravenously or per rectum if intravenous access is not possible.

5.9 Example 9

Apoptosis Promoting Activity of DIM and Antiprotazoal Compounds in a Cell Culture Models of Malaria, Trypanosomiasis, Leishmaniasis, Cryptospridiosis, Trichomonaiasis and Blastocystosis Introduction: Cell culture techniques relevant to human protozoal infections include methods developed to test anti-protozoal agents in models of the blood stage of malaria, models of macrophage infection with amastigotes of *Leishmania*, models of macrophage infection with Trypanosomes, models of enterocyte infection with *Cryptosporidium*, models of infection with *Trichomonas*, and models of enterocyte infection with *Blastocystis Hominis*. Preferred methods allow culture conditions and testing for the cell death response induced by the anti-protazoal agent(s) attributable to apoptosis. Testing of a DIM-related indole alone to establish the minimum effective concentration in culture media and the concentration from reduction of infected cell number by 50% ($EC_{50}$) is conducted. The combination of one or more anti-protozoal agents in combination with a DIM-related indole is used to establish additive or synergistic activity according to established methods (Nduat, 2006, Acta Trop. 97(3):357-63).

The relevant in vitro culture and endpoint assay methods for use with DIM-related indoles alone and in combination are listed in the following chart.

| Parasite | Culture Methods | Assay Methods (Ref) |
|---|---|---|
| *Plasmodium* Species | *P. falciparum* in human RBC's | Giemsa-staining RBC's (1, 2) |
| *Trypanosome* Species | *T Cruzi* or *T. brucie* in media | Alamar Blue Florometric dye (3, 4) |
| *Leishmania* Species | *L. donovani* in media | Alamar Blue Florometric dye (4) |
| *Cryptosporidium* Species | H69 Human Bile Duct Cells | DAPI staining for apoptosis (5) |
| *Blastocystis Hominis* | Culture of *B. Hominis* in media. | Phase contrast microscopy and flow cytometry (6) |
| *Trichomonas vaginalis* | Culture of *T. Vaginalis* in media | Aerobic and anerobic culture with inverted phase contrast microscopy (7) |

References for In Vitro Methods

1. Kumar R, Musiyenko A, Barik S. The heat shock protein 90 of *Plasmodium falciparum* and antimalarial activity of its inhibitor, geldanamycin. Malar J. 2003 Sep. 15; 2:30.
2. Trager W, Jensen J B. Human malaria parasites in continuous culture. 1976. J Parasitol. 2005 June; 91(3):484-6.
3. X. Verma N K, Dey C S. Possible mechanism of miltefosine-mediated death of *Leishmania donovani*. Antimicrob Agents Chemother. 2004 August; 48(8):3010-5
4. Tasdemir D, Kaiser M, Brun R, Yardley V, Schmidt T J, Tosun F, Ruedi P. Antitrypanosomal and antileishmanial activities of flavonoids and their analogues: in vitro, in vivo, structure-activity relationship, and quantitative structure-activity relationship studies. Antimicrob Agents Chemother. 2006 April; 50(4):1352-64.
5. Chen X M, Gores G J, Paya C V, LaRusso N F. *Cryptosporidium parvum* induces apoptosis in biliary epithelia by a Fas/Fas ligand-dependent mechanism. Am J Physiol. 1999 September; 277(3 Pt 1):G599-608
6. Ho L C, Singh M, Suresh G, Ng G C, Yap E H. Axenic culture of *Blastocystis hominis* in Iscove's modified Dulbecco's medium. Parasitol Res. 1993; 79(7):614-6.
7. Crowell A L, Sanders-Lewis K A, Secor W E. In vitro metronidazole and tinidazole activities against metronidazole-resistant strains of *Trichomonas vaginalis*. Antimicrob Agents Chemother. 2003 April; 47(4): 1407-9.

Established methods are utilized to demonstrate additive and synergistic interaction of DIM-related indoles and additional antiprotozoal agents including methods established for *P. Falciparum*. (Gupta et al., 2002, Antimicrob Agents Chemother. 46(5):1510-5).

Examples of the agent(s) to be tested, both alone and in combination, for each species of protozoan parasite most appropriate for the methods and compositions of the present invention are summarized in the following five tables:

| I. *Plasmodium* Species (*P. Falciparum, P. Ovale, P. Vivex*) | | |
|---|---|---|
| Class of Agent | Example of Agent | Concentration Range |
| DIM-related indole | 3,3'-Diindolylmethane | .01-50 Micromolar |
| Artimisinin derivative | Artesunate | .001-10 Micromolar |
| Curcumin or derivative | Curcumin | .01-50 Micromolar |
| Choloriquine | Chloroquine | .001-20 Micromolar |
| Quinine | Primaquine | .001-20 Micromolar |

-continued

I. *Plasmodium* Species (*P. Falciparum, P. Ovale, P. Vivex*)

| Class of Agent | Example of Agent | Concentration Range |
|---|---|---|
| Jasmonate | Methyl jasmonate | .01-50 Micromolar |
| Antibiotic | Clindamycin | .001-20 Micromolar |

II. *Leishmania* Species (*L. donovani, L. tropica*)

| Class of Agent | Example of Agent | Concentration Range |
|---|---|---|
| DIM-related indole | 3,3'-Diindolylmethane | .01-50 Micromolar |
| miltefosine | miltefosine | .01-50 Micromolar |
| Pentavalent Antimony | Sodium stibogluconate | .01-50 Micromolar |
| Amphotericin B | Amphotericin B | .001-20 Micromolar |
| Pentamidine | Pentamidine | .001-20 Micromolar |
| Campothectins | Topotecan | .01-50 Micromolar |

III. *Trypanosome* Species (*T. brucei, T. brucei gambiense, T. cruzi*)

| Class of Agent | Example of Agent | 'Concentration Range |
|---|---|---|
| DIM-related indole | 3,3'-Diindolylmethane | .01-50 Micromolar |
| Nifurtimox | Nifurtimox | .001-20 Micromolar |
| Benznidazole | Benznidazole | .001-20 Micromolar |
| Arsenicals | Melarsoprol | .001-20 Micromolar |
| Campothectins | topotecan | .001-20 Micromolar |
| Ornithine decarboxylase Inhibitor | eflornithine | .001-20 Micromolar |

IV. *Cryptosporidium* Species (*C. parvum, C. hominis*)

| Class of Agent | Example of Agent | Concentration Range |
|---|---|---|
| DIM-related indole | 3,3'-Diindolylmethane | .01-50 Micromolar |
| Nitazoxanine | Nitazoxanine | .001-20 Micromolar |
| Curcumin | Curcumin | .01-50 Micromolar |
| Artemisinin | Artusenate | .001-20 Micromolar |
| Flavonoid | Genistein | .01-50 Micromolar |

V. *Blastocystis Hominis*

| Class of Agent | Example of Agent | Concentration Range |
|---|---|---|
| DIM-related indole | 3,3'-Diindolylmethane | .01-50 Micromolar |
| Curcumin | Curcumin | .01-50 Micromolar |
| Artemisinin | Artusenate | .001-20 Micromolar |

VI. *Trichomonas Vaginalis*

| Class of Agent | Example of Agent | Concentration Range |
|---|---|---|
| DIM-related indole | 3,3'-Diindolylmethane | .01-50 Micromolar |
| Curcumin | Curcumin | .01-50 Micromolar |
| Artemisinin | Artusenate | .001-20 Micromolar |
| Nitroimidazole | Metronidazole | .001-20 Micromolar |
| Nitroimidazole | Tinidazole | .001-20 Micromolar |

Expected results include the demonstration of antiprotozoal activity of DIM-related indoles that is amplified when combined with selected antiprotozoal agent(s).

5.10 Example 10

Use of DIM Alone and in Combination with Agents Using In Vivo Models of Malaria In malaria, sporozoites from the mosquito salivary glands rapidly enter the circulation after a bite and localize in hepatocytes where they multiply and develop into tissue schizonts. During this asymptomatic tissue stage the sporozoites traverse through and damage multiple hepatocytes, yet the final infected hepatocyte has been shown to become resistant to apoptosis associated with the presence of the sporozoite. Anti-malarial activity against the primary liver stage is limited to a few of the known anti-protozoal drugs and has been limited to *P. falciparum*. The Atovaquone-Proguanil combination drug, Malarone, and Primaquine show anti-liver stage activity but are expensive. Additional treatments active against liver stage infection are needed. Animal models using *Plasmondium berghei* sporozoites (Anka) in mice have developed to test postential treatments for the liver stage following infection of the animals with sporozoites (van de Sand et al., 2005, Mol Microbiol. 58(3):731-42). Methods from this animal model are adapted to demonstrate the in vivo activity of DIM-related indoles against the liver stage of *plasmodium* infection. In addition this model lends itself to demonstration of the induction of apoptosis in infected hepatocytes by DIM, the DIM-Artuscenate Combination, and the oral use of DIM-Atuscenate-Curcumin, as well as other DIM-related indole anti-protozoal combinations.

Briefly, the following method is used in mice to assay for sporozoite infectivity and hepatic infection in vivo. Female Swiss Webster mice, 5 to 6 weeks old, are injected intravenously (i.v.) or intraperitoneally (i.p.) with DIM-related indole, alone or in combination with one or more anti-protozoal agents, 60 min, 30 min, before i.v. injection of $10^4$ *P. berghei* sporozoites. Forty hours later, livers are harvested, total RNA is isolated, and malaria infection is quantified using reverse transcription followed by real-time PCR with primers that recognize *P. yoelii*-specific sequences within the 18S rRNA as previously described (Bruna-Romero et al., 2001, Int. J. Parasitol. 31:1499-1502). All in vivo data are analyzed using the Student t test for unpaired samples. Typically, all experiments are performed twice with six mice per group per experiment.

In vivo models have also been established to test for erythrocytic antimalarial activities of DIM-related indoles using the *Plasmodium vinckei petteri* (279BY) strain and the *Plasmodium yoelii nigeriensis* strain in female Swiss mice (Singh et al., 2000, Acta Trop. 77(2):185-93). These methods are modified for intraperitoneal (i.p.) and oral administration of DIM-related indoles alone or in combination with other antimalarial agents. Drugs are injected i.p. or orally in 100 μl of DMSO. Parasitemia levels are monitored in Giemsa-stained blood smears, and blood samples are collected for determination of infection on a fluorescence-activated cell sorter (Barkan et al., 2000, Int J Parasitol. 30(5):649-53).

In testing in mice the following additional method is used to assay for efficacy of a DIM-related indole, alone or in combination with an anti-protozoal agent, against erythrocytic stages in vivo. The standard 4-day suppression test is used to assess the efficacy of DIM and DIM combinations against malaria erythrocytic stages in vivo (Peters, 1975, Ann. Trop. Med. Parasitol. 69:155-171). Female Swiss Webster mice, 5 to 6 weeks old, are injected i.v. with $2 \times 10^5$ GFP-expressing *P. berghei* parasites, and 1 h later mice are injected i.v. with DIM, DIM plus a second agent, or buffer for control group. Mice are treated with DIM, DIM plus a second agent, or buffer once daily for an additional 3 days. For the experiments in DIM or DIM in combination with a second agent, the test compounds are administered orally or parenterally, Swiss Webster mice are infected with GFP-expressing parasites as above, and 1 h later, DIM, or DIM plus a second agent, or water alone was administered by gavage. Following treatment, survival of the mice is monitored and parasitemia is determined by fluorescence-activated cell sorting (FACS) analysis. For FACS, 2 µl of blood is diluted in 1 ml PBS containing 1% fetal calf serum and 0.01% $NaN_3$, and the number of fluorescent cells is determined for example using the FACS Calibur System with CellQuest Software (Becton Dickinson). Statistical significance is determined using the Student t test for unpaired samples. All experiments are performed twice with five mice per group per experiment.

The treatment groups and dose ranges for in vivo testing of DIM-related indoles and complementary anti-protozoal agents in mice include the following:

| Antiprotozoal Agent | Dose Range | Route |
|---|---|---|
| DIM | 50-500 mg/kg/day | Oral, i.p.*, i.v.** |
| Artesunate | 1-100 mg/kg/day | Oral, i.p.*, i.v.** |
| Artemether | 1-100 mg/kg/day | Oral, i.p.*, i.v.** |
| Dihydroartimisinin | 1-100 mg/kg/day | Oral, i.p.*, i.v.** |
| Chloroquine | 1-50 mg/kg/day | Oral, i.p.*, i.v.** |
| Atovoquone | 1-50 mg/kg/day | Oral, i.p.*, i.v.** |
| Quinine | 1-50 mg/kg/day | Oral, i.p.*, i.v.** |
| Primaquine | 1-50 mg/kg/day | Oral, i.p.*, i.v.** |
| Proguanil | 1-50 mg/kg/day | Oral, i.p.*, i.v.** |
| Curcumin | 50-500 mg/kg/day | Oral |

*i.p. = intraperitoneal;
**i.v.= intravenous

5.11 Example 11

Use of the Combination of DIM, Artemesinin, and Cucurmin In HIV-Associated *Cryptosporidium* Infection

*Cryptosporidium* sp. has been reported worldwide, especially infecting immunocompromised persons and in immunocompetent persons having contact with cattle. In individuals infected with human immunodeficiency virus (HIV), many will have cryptosporidiosis when diagnosed with HIV infection and more will develop it later in the course of their disease. No specific effective treatment exists for cryptosporidiosis, and an intact immune system is the major factor to resolve the infection. New approaches for the treatment of cryptosporidiosis are needed, since many symptomatic HIV infected patients do not have access to highly active antiretroviral therapy (HAART). HIV infected patients with adequate CD4 lymphocyte counts are reluctant to start HAART for the isolated complaint of diarrhea. DIM-related indole therapy offers a new therapeutic option for this common parasitic infection in both HIV positive and negative individuals.

In this example of human use of oral DIM-based antiprotozoal treatment, an HIV positive male with chronic diarrhea will be treated with capsules containing absorption-enhanced DIM, Artemesinin, Curcumin, and piperine (Example 6.2). The subject is not on anti-retroviral therapy and his CD4 lymphocyte count is greater than 200. He complains of chronic diarrhea with 3-4 unformed, watery stools daily for 1 month. Stool analysis reveals oocysts of *cryptosporidium hominis/parvum*. Following use of 2-4 capsules twice daily of the DIM/Artemesinin/Cucurmin mixture, improvement in diarrhea is expected. After 1 month of therapy it is expected that symptoms will resolve with resumption of a normal stool pattern and a repeat stool analysis will reveal no cryptosporidial oocysts. A similar approach to treatment is used in HIV positive and negative individuals infected with *Cyclospora, Isospora belli*, or *Cystoisospora*.

What is claimed is:

1. A method of treating Chagas disease or an infection caused by *Trypanosoma Cruzi*, comprising administering to a subject in need thereof an effective amount of a DIM-related indole.

2. The method of claim 1, wherein the subject is a human.

3. The method of claim 1, wherein the DIM-related indole is selected from the group consisting of:

a compound of formula I:

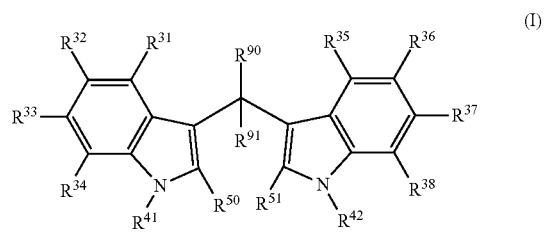

wherein $R^{32}$ and $R^{36}$ are substituents independently selected from the group consisting of hydrogen, hydroxyl, and methoxy, and ethoxycarbonyl groups, $R^{33}$ and $R^{37}$ are substituents independently selected from the group consisting of hydrogen, hydroxyl, and methoxy, $R^{31}$, $R^{34}$, $R^{35}$, $R^{38}$, $R^{41}$, and $R^{42}$ are hydrogen, $R^{50}$, $R^{51}$ are either hydrogen or methyl, and $R^{90}$, $R^{91}$ are hydrogen;

a compound of formula II:

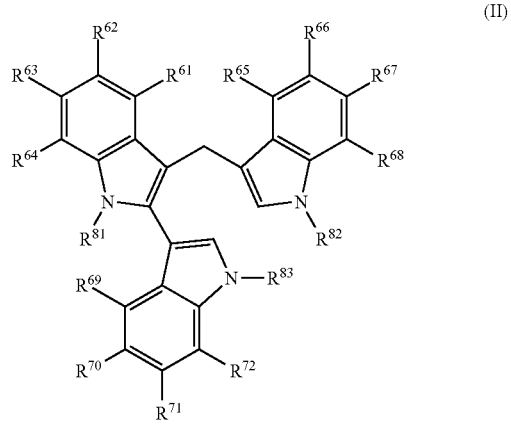

wherein $R^{62}$, $R^{63}$, $R^{66}$, $R^{67}$, $R^{70}$, and $R^{71}$ are substituents independently selected from the group consisting of hydrogen, hydroxyl, and methoxy, and $R^{61}$, $R^{64}$, $R^{65}$, $R^{68}$, $R^{69}$, $R^{72}$, $R^{81}$, $R^{82}$, and $R^{83}$ are hydrogen;

a compound of formula (IV):

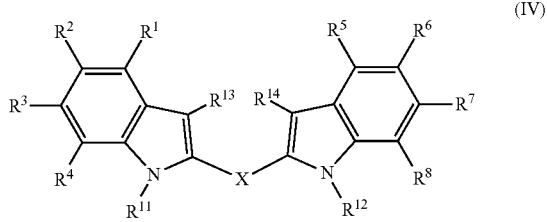

wherein $R^1$, $R^2$, $R^3$, $R^4$, $R^5$, $R^6$, $R^7$, and $R^8$ are substituents independently selected from the group consisting of hydrogen, $C_1$-$C_{24}$ alkyl, $C_2$-$C_{24}$ alkenyl, $C_2$-$C_{24}$ alkynyl, $C_5$-$C_{20}$ aryl, $C_6$-$C_{24}$ alkaryl, $C_6$-$C_{24}$ aralkyl, halo, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl, acyloxy, $C_2$-$C_{24}$ alkoxycarbonyl, $C_6$-$C_{20}$ aryloxycarbonyl, halocarbonyl, $C_2$-$C_{24}$ alkylcarbonato, $C_6$-$C_{20}$ arylcarbonato, carboxy, carboxylato, carbamoyl, mono-($C_1$-$C_{24}$ alkyl)-substituted carbamoyl, di-($C_1$-$C_{24}$ alkyl)-substituted carbamoyl, mono-substituted arylcarbamoyl, thiocarbamoyl, carbamido, cyano, isocyano, cyanato, isocyanato, isothiocyanato, azido, formyl, thioformyl, amino, mono- and di-($C_1$-$C_{24}$ alkyl)-substituted amino, mono- and di-($C_5$-$C_{20}$ aryl)-substituted amino, $C_2$-$C_{24}$ alkylamido, $C_5$-$C_{20}$ arylamido, imino, allkylimino, arylimino, nitro, nitroso, sulfo, sulfonato, $C_1$-$C_{24}$ alkylsulfanyl, arylsulfanyl, $C_1$-$C_{24}$ afkylsulfinyl, $C_5$-$C_{20}$ arylsulfinyl, $C_1$-$C_{24}$ alkylsulfonyl, $C_5$-$C_{20}$ arylsulfonyl, phosphono, phosphonato, phosphinato, phospho, phosphino, and combinations thereof, and further wherein any two adjacent (ortho) substituents may be linked to form a cyclic structure selected from five-membered rings, six-membered rings, and fused five-membered and/or six-membered rings, wherein the cyclic structure is aromatic, alicyclic, heteroaromatic, or heteroalicyclic, and has zero to 4 non-hydrogen substituents and zero to 3 heteroatoms, with the proviso that one but not both of $R^2$ and $R^6$ is amino, mono-substituted amino, or di-substituted amino;

$R^{11}$ and $R^{12}$ are independently selected from the group consisting of hydrogen, $C_1$-$C_{24}$ alkyl, $C_2$-$C_{24}$ alkoxycarbonyl, amino-substituted $C_1$-$C_{24}$ alkyl, ($C_1$-$C_{24}$ alkylamino)-substituted $C_1$-$C_{24}$ alkyl, and di-($C_1$-$C_{24}$ alkyl)amino-substituted $C_1$-$C_{24}$ alkyl, $R^{13}$ and $R^{14}$ are defined as for $R^1$, $R^2$, $R^3$, $R^4$, $R^5$, $R^6$, $R^7$, and $R^8$, with the proviso that at least one of $R^{13}$ and $R^{14}$ is other than hydrogen, and X is O, S, arylene, heteroarylene, $CR^{15}R^{16}$ or $NR^{17}$ wherein $R^{15}$ and $R^{16}$ are hydrogen, $C_1$-$C_6$ alkyl, or together form $=CR^{18}R^{19}$ where $R^{18}$ and $R^{19}$ are hydrogen or $C_1$-$C_6$ alkyl, and $R^{17}$ is as defined for $R^{11}$ and $R^{12}$; and a compound of formula (V):

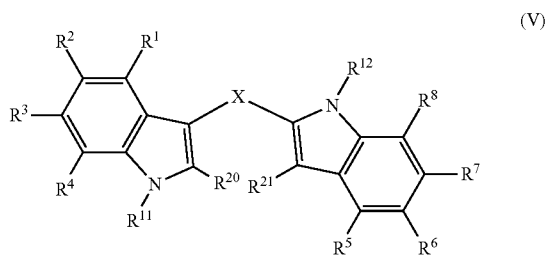

wherein $R^1$, $R^2$, $R^3$, $R^4$, $R^5$, $R^6$, $R^7$, and $R^8$ are substituents independently selected from the group consisting of hydrogen, $C_1$-$C_{24}$ alkyl, $C_2$-$C_{24}$ alkenyl, $C_2$-$C_{24}$ alkynyl, $C_5$-$C_{20}$ aryl, $C_6$-$C_{24}$ alkaryl, $C_6$-$C_{24}$ aralkyl, halo, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl, acyloxy, $C_2$-$C_{24}$ alkoxycarbonyl, $C_6$-$C_{20}$ aryloxycarbonyl, halocarbonyl, $C_2$-$C_{24}$ alkylcarbonato, $C_6$-$C_{20}$ arylcarbonato, carboxy, carboxylato, carbamoyl, mono-($C_1$-$C_{24}$ alkyl)-substituted carbamoyl, di-($C_1$-$C_{24}$ alkyl)-substituted carbamoyl, mono-substituted arylcarbamoyl, thiocarbamoyl, carbamido, cyano, isocyano, cyanato, isocyanato, isothiocyanato, azido, formyl, thioformyl, amino, mono- and di-($C_1$-$C_{24}$ alkyl)-substituted amino, mono- and di-($C_5$-$C_{20}$ aryl)-substituted amino, $C_2$-$C_{24}$ alkylamido, $C_6$-$C_{20}$ arylamido, imino, alkylimino, arylimino, nitro, nitroso, sulfo, sulfonato, $C_1$-$C_{24}$ alkylsulfanyl, arylsutfanyl, $C_1$-$C_{24}$ alkylsulfinyl, $C_5$-$C_{20}$ arylsulfinyl, $C_1$-$C_{24}$ alkylsulfonyl, $C_5$-$C_{20}$ arylsulfonyl, phosphono, phosphonato, phosphinato, phospho, phosphino, and combinations thereof, and further wherein any two adjacent (ortho) substituents may be linked to form a cyclic structure selected from five-membered rings, six-membered rings, and fused five-membered and/or six-membered rings, wherein the cyclic structure is aromatic, alicyclic, heteroaromatic, or heteroalicyclic, and has zero to 4 non-hydrogen substituents and zero to 3 heteroatoms, and $R^{11}$ and $R^{12}$ are independently selected from the group consisting of hydrogen, $C_1$-$C_{24}$ alkyl, $C_2$-$C_{24}$ alkoxycarbonyl, amino-substituted $C_1$-$C_{24}$ alkyl, ($C_1$-$C_{24}$ alkylamino)-substituted $C_1$-$C_{24}$ alkyl, and di-($C_1$-$C_{24}$ alkyl) amino-substituted $C_1$-$C_{24}$ alkyl, with the provisos that at least one of $R^1$, $R^2$, $R^4$, $R^5$, $R^6$, $R^7$, $R^8$, $R^{11}$ and $R^{12}$ is other than hydrogen, and when $R^1$, $R^2$, $R^3$, $R^4$, $R^5$, $R^6$, $R^7$, and $R^8$ are selected from hydrogen, halo, alkyl and alkoxy, then $R^{11}$ and $R^{12}$ are other than hydrogen and alkyl; and $R^{20}$ and $R^{21}$ are defined as for $R^1$, $R^2$, $R^3$, $R^4$, $R^5$, $R^6$, $R^7$, and $R^8$.

4. The method of claim 1, wherein the DIM-related indole is selected from the group consisting of: diindolylmethane (DIM), hydoxylated DIMs, methoxylated DIMs, 2-(Indol-3-ylmethyl)-3,3'-diindolylmethane (LTR), hydroxylated LTRs, methoxylated LTRs, 5,5'-dimethylDIM (5-Me-DIM), 2,2'-dimethylDIM (2-Me-DIM), 5,5'-dichloroDIM (5-Cl-DM), imidazolelyl-3,3'-diindolylmethane, nitro-substituted imidazolelyl-3,3'-diindolylmethanes, 2,10-dicarbethoxy-6-methoxy-5,7-dihydro-indolo-[2,3-b]carbazole, 6-ethoxycarbonyloxy-5,7-dihydro-indolo-[2,3-b]carbazole and 2,10-dicarbethoxy-6-ethoxycarbonyloxy-5,7-dihydro-indolo-[2,3-b]carbazole, 2,6-dicarbethoxy-3,3'-dimethyl-13,14-diindolylmethane and indole-3-carbinol.

5. The method of claim 1, wherein the DIM-related indole is DIM.

6. The method of claim 5, wherein the DIM is processed DIM.

7. The method of claim 4, wherein the DIM-related indole is microencapsulated with phosphatidylcholine (PC), complexed with PC, or made into rapidly dissolving microparticles and nanoparticles.

8. The method of claim 1, wherein the DIM-related indole is administered intravenously or orally.

9. The method of claim 5, wherein the DIM is formulated as a suspension or emulsion and administered intravenously in an amount of: (i) 2-15 mg/kg per dose every 8 to 12 hours, or (ii) 0.5-15 mg/kg per day.

10. The method of claim 5, wherein the DIM is formulated for enhanced absorption and administered orally in a dose of 0.5-12 mg/kg per day.

11. The method of claim 5, wherein the DIM is formulated as a suppository and administered rectally in a dose of 0.5-12 mg/kg per day.

12. The method of claim 5, wherein the DIM is administered orally in an amount from 10 to 300 mg per dose.

13. The method of claim 5, wherein the DIM is administered in an absorption enhancing formulation in an amount of 25 to 750 mg per day as a suspension of microparticles in a starch carrier matrix.

14. The method of claim 1, wherein the DIM-related indole is administered orally in an absorption enhancing formulation at a dose of 50 to 250 mg/day.

15. The method of claim 6, wherein the processed DIM is administered orally in a capsule comprising 150 to 300 mg of processed DIM.

16. The method of claim 1, wherein the DIM-related indole is administered in an oral suspension in an amount of 3 to 10 mg/kg/dose twice daily.

17. The method of claim 1, wherein the DIM-related indole is administered alone without an additional anti-protozoal agent.

18. The method of claim 1, further comprising administering to the subject an anti-protozoal agent.

19. The method of claim 18, wherein the anti-protozoal agent is suranim, nifurtimox, bensnidazole, a campothectin, melarsoprol, pentamidine or eflornithine.

20. The method of claim 18, wherein the DIM-related indole is administered intravenously or orally.

21. The method of claim 19, wherein the anti-protozoal agent is nifurtimox or benznidazole, and wherein nifurtimox or benznidazole is administered orally.

22. The method of claim 18, wherein the DIM-related indole is administered orally in a dose of 0.5-12 mg/kg per day or intravenously in a dose of 0.5-15 mg/kg per day, and wherein the anti-protozoal agent is: (i) suranim or a campothectin administered intravenously, or (ii) nifurtimox or bensnidazole administered orally; and wherein the DIM-related indole is selected from the group consisting of:
diindolylmethane (DIM), hydoxylated DiMs, methoxylated DIMs, 2-(Indol-3-ylmethyl)-3,3'-diindolylmethane (LTR), hydroxylated LTRs, methoxylated LTRs, 5,5'-dimethylDIM (5-Me-DIM), 2,2'-dimethylDIM (2-Me-DIM), 5,5'-dichloroDIM (5-Cl-DIM), imidazolelyl-3,3'-diindolylmethane, nitro-substituted imidazolelyl-3,3'-diindolylmethanes, 2,10-dicarbethoxy-6-methoxy-5,7-dihydro-indolo-[2,3-b]carbazole, 6-ethoxycarbonyloxy-5,7-dihydro-indolo-[2,3-b] carbazole and 2,10-dicarbethoxy-6-ethoxycarbonyloxy-5,7-dihydro-indolo-[2,3-b] carbazole, 2,6-dicarbethoxy-3,3'-dimethyl-13,14-diindolylmethane and indole-3-carbinol.

23. A kit comprising: (i) a DIM-related indole formulated for oral or intravenous administration, and (ii) an anti-protozoal agent, wherein the anti-protozoal agent is nifurtimox or benznidazole and wherein the anti-protozoal agent is formulated for oral administration.

24. The kit of claim 23, wherein the DIM-related indole is in n amount effective to inhibit the growth of *Trypanosoma Cruzi*.

25. The kit of claim 23, wherein the DIM-related indole is selected from the group consisting of:
a compound of formula I:

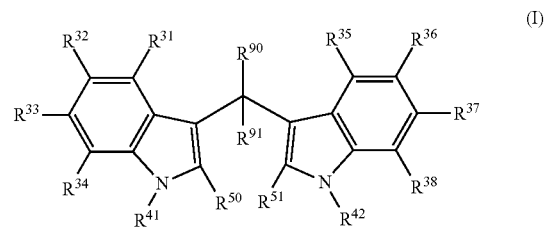

wherein $R^{32}$ and $R^{36}$ are substituents independently selected from the group consisting of hydrogen, hydroxyl, and methoxy, and ethoxycarbonyl groups, $R^{33}$ and $R^{37}$ are substituents independently selected from the group consisting of hydrogen, hydroxyl, and methoxy,
$R^{31}$, $R^{34}$, $R^{35}$, $R^{38}$, $R^{41}$, and $R^{42}$ are hydrogen,
$R^{50}$, $R^{51}$ are either hydrogen or methyl, and
$R^{90}$, $R^{91}$ are hydrogen;
a compound of formula II:

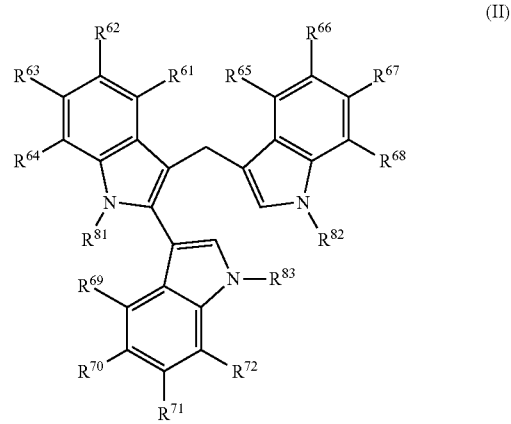

wherein $R^{62}$, $R^{63}$, $R^{66}$, $R^{67}$, $R^{70}$, and $R^{71}$ are substituents independently selected from the group consisting of hydrogen, hydroxyl, and methoxy, and
$R^{61}$, $R^{64}$, $R^{65}$, $R^{68}$, $R^{69}$, $R^{72}$, $R^{81}$, $R^{82}$ and $R^{83}$ are hydrogen;
a compound of formula (IV):

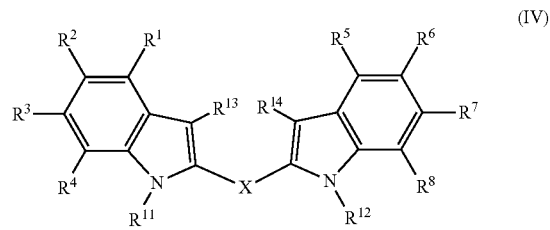

wherein $R^1$, $R^2$, $R^3$, $R^4$, $R^5$, $R^6$, $R^7$, and $R^8$ are substituents independently selected from the group consisting of hydrogen, $C_1$-$C_{24}$ alkyl, $C_2$-$C_{24}$ alkenyl, $C_2$-$C_{24}$ alkynyl, $C_5$-$C_{20}$ aryl, $C_6$-$C_{24}$ alkaryl, $C_2$-$C_{24}$ aralkyl, halo, hydroxyl, sulfhydryl, $C_1$-$C_{24}$ alkoxy, $C_2$-$C_{24}$ alkenyoxy, $C_2$-$C_{24}$ alkynyloxy, $C_5$-$C_{20}$ aryloxy, acyl, acyloxy, $C_2$-$C_{24}$ alkoxycarbonyl, $C_6$-$C_{20}$ aryloxycarbonyl, halocarbonyl, $C_2$-$C_{24}$ alkylcarbonato, $C_6$-$C_{20}$ arylcarbonato, carboxy, carboxylato, carbamoyl, mono-($C_1$-$C_{24}$ alkyl)-substituted carbamoyl, di-($C_1$-$C_{24}$ alkyl)-substituted carbamoyl, mono-substituted arylcarbamoyl, thiocarbamoyl, carbamido, cyano, isocyano, cyanato, isocyanato, isothiocyanato, azido, formyl, thioformyl, amino, mono- and di-($C_1$-$C_{24}$ alkyl)-substituted amino, mono- and di-($C_5$-$C_{20}$ aryl)-substituted amino, $C_2$-$C_{24}$ alkylamido, $C_5$-$C_{20}$ arylamido, imino, alkylimino, arylimino, nitro, nitroso, sulfo, sulfonato, $C_1$-$C_{24}$ alkylsulfanyl,

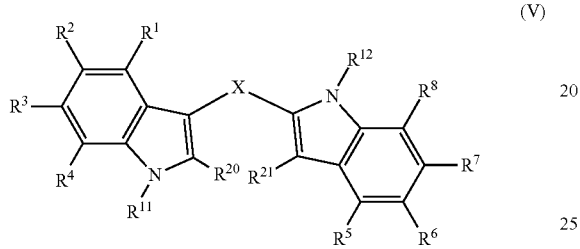

(V)

wherein $R^1$, $R^2$, $R^3$, $R^4$, $R^5$, $R^6$, $R^7$, and $R^8$ are substituents independently selected from the group consisting of hydrogen, $C_1$-$C_{24}$ alkyl, $C_2$-$C_{24}$ alkenyl, $C_2$-$C_{24}$ alkynyl, $C_5$-$C_{20}$ aryl, $C_6$-$C_{24}$ alkaryl, $C_6$-$C_{24}$ aralkyl, halo, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl, acyloxy, $C_2$-$C_{24}$ alkoxycarbonyl, $C_6$-$C_{20}$ aryloxycarbonyl, halocarbonyl, $C_2$-$C_{24}$ alkylcarbonato, $C_6$-$C_{20}$ arylcarbonato, carboxy, carboxylato, carbamoyl, mono-($C_1$-$C_{24}$ alkyl)-substituted carbamoyl, di-($C_1$-$C_{24}$ alkyl)-substituted carbamoyl, mono-substituted arylcarbamoyl, thiocarbamoyl, carbamido, cyano, isocyano, cyanato, isocyanato, isothiocyanato, azido, formyl, thioformyl, amino, mono- and di-($C_1$-$C_{24}$ alkyl)-substituted amino, mono- and di-($C_5$-$C_{20}$ aryl)-substituted amino, $C_2$-$C_{24}$ alkylamido, $C_6$-$C_{20}$ arylamido, imino, alkylimino, arylimino, nitro, nitroso, sulfo, sulfonato, $C_1$-$C_{24}$ alkylsulfanyl, arylsulfanyl, $C_1$-$C_{24}$ alkylsulfinyl, $C_5$-$C_{20}$ arylsulfinyl, $C_1$-$C_{24}$ alkylsulfonyl, $C_5$-$C_{20}$ arylsulfonyl, phosphono, phosphonato, phosphinato, phospho, phosphino, and combinations thereof, and further wherein any two adjacent (ortho) substituents may be linked to form a cyclic structure selected from five-membered rings, six-membered rings, and fused five-membered and/or six-membered rings, wherein the cyclic structure is aromatic, alicyclic, heteroaromatic, or heteroalicyclic, and has zero to 4 non-hydrogen substituents and zero to 3 heteroatoms, and $R^{11}$ and $R^{12}$ are independently selected from the group consisting of hydrogen, $C_1$-$C_{24}$ alkyl, $C_2$-$C_{24}$ alkoxycarbonyl, amino-substituted $C_1$-$C_{24}$ alkyl, ($C_1$-$C_{24}$ alkylamino)-substituted $C_1$-$C_{24}$ alkyl, and di-($C_1$-$C_{24}$ alkyl)amino-substituted $C_1$-$C_{24}$ alkyl, with the provisos that at least one of $R^1$, $R^2$, $R^3$, $R^4$, $R^5$, $R^6$, $R^7$, $R^8$, $R^{11}$ and $R^{12}$ is other than hydrogen, and when $R^1$, $R^2$, $R^3$, $R^4$, $R^5$, $R^6$, $R^7$ and $R^8$ are selected from arylsulfanyl, $C_1$-$C_{24}$ afkylsulfinyl, $C_5$-$C_{20}$ arylsulfinyl, $C_1$-$C_{24}$ alkylsulfonyl, $C_5$-$C_{20}$ arylsulfonyl, phosphono, phosphonato, phosphinato, phospho, phosphino, and combinations thereof, and further wherein any two adjacent (ortho) substituents may be linked to form a cyclic structure selected from five-membered rings, six-membered rings, and fused five-membered and/or six-membered rings, wherein the cyclic structure is aromatic, alicyclic, heteroaromatic, or heteroalicyclic, and has zero to 4 non-hydrogen substituents and zero to 3 heteroatoms, with the proviso that one but not both of $R^2$ and $R^6$ is amino, mono-substituted amino, or di-substituted amino;

$R^{11}$ and $R^{12}$ are independently selected from the group consisting of hydrogen, $C_1$-$C_{24}$ alkyl, $C_2$-$C_{24}$ alkoxycarbon, amino-substituted $C_1$-$C_{24}$ alkyl, ($C_1$-$C_{24}$ alkylamino)-substituted $C_1$-$C_{24}$ alkyl, and di-($C_1$-$C_{24}$ alkyl)amino-substituted $C_1$-$C_{24}$ alkyl, $R^{13}$ and $R^{14}$ are defined as for $R^1$, $R^2$, $R^3$, $R^4$, $R^5$, $R^6$, $R^7$, and $R^8$, with the proviso that at least one of $R^{13}$ and $R^{14}$ is other than hydrogen, and X is O, S, arylene, heteroarylene, $CR^{15}R^{16}$ or $NR^{17}$ wherein $R^{15}$ and $R^{16}$ are hydrogen, $C_1$-$C_6$ alkyl, or together form $=CR^{18}R^{19}$ where $R^{18}$ and $R^{19}$ are hydrogen or $C_1$-$C_6$ alkyl, and $R^{17}$ is as defined for $R^{11}$ and $R^{12}$; and a compound of formula (V):

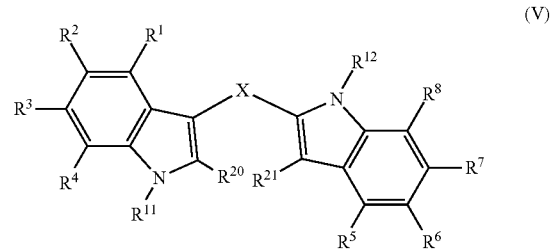

(V)

wherein $R^1$, $R^2$, $R^3$, $R^4$, $R^5$, $R^6$, $R^7$, and $R^8$ are substituents independently selected from the group consisting of hydrogen, $C_1$-$C_{24}$ alkyl, $C_2$-$C_{24}$ alkenyl, $C_2$-$C_{24}$ alkynyl, $C_5$-$C_{20}$ aryl, $C_6$-$C_{24}$ alkaryl, $C_6$-$C_{24}$ aralkyl, halo, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl, acyloxy, $C_2$-$C_{24}$, alkoxycarbonyl, $C_6$-$C_{20}$ aryloxycarbonyl, halocarbonyl, $C_2$-$C_{24}$ alkylcarbonato, $C_6$-$C_{20}$ arylcarbonato, carboxy, carboxylato, carbamoyl, mono-($C_1$-$C_{24}$ alkyl)-substituted carbamoyl, di-($C_1$-$C_{24}$ alkyl)-substituted carbamoyl, mono-substituted arylcarbamoyl, thiocarbamoyl, carbamido, cyano, isocyano, cyanato, isocyanato, isothiocyanato, azido, formyl, thioformyl, amino, mono- and di-($C_1$-$C_{24}$ alkyl)-substituted amino, mono- and di-($C_5$-$C_{20}$ aryl)-substituted amino, $C_2$-$C_{24}$ alkylamido, $C_6$-$C_{20}$ arylamido, imino, alkylimino, arylimino, nitro, nitroso, sulfo, sulfonato, $C_1$-$C_{24}$ alkylsulfanyl, arylsulfanyl, $C_1$-$C_{24}$ alkylsulfinyl, $C_5$-$C_{20}$ arylsulfinyl, $C_1$-$C_{24}$ alkylsulfonyl, $C_5$-$C_{20}$ arylsulfonyl, phosphono, phosphonato, phosphinato, phospho, phosphino, and combinations thereof, and further wherein any two adjacent (ortho) substituents may be linked to form a cyclic structure selected from five-membered rings, six-membered rings, and fused five-membered and/or six-membered rings, wherein the cyclic structure is aromatic, alicyclic, heteroaromatic, or heteroalicyclic, and has zero to 4 non-hydrogen substituents and zero to 3 heteroatoms, and $R^{11}$ and $R^{12}$ are independently selected from the group consisting of hydrogen, $C_1$-$C_{24}$ alkyl, $C_2$-$C_{24}$ alkoxycarbonyl, amino-substituted $C_1$-$C_{24}$ alkyl, ($C_1$-$C_{24}$ alkylamino)-substituted $C_1$-$C_{24}$ alkyl, and di-($C_1$-$C_{24}$ alkyl)amino-substituted $C_1$-$C_{24}$ alkyl, with the provisos that at least one of $R^1$, $R^2$, $R^3$, $R^4$, $R^5$, $R^6$, $R^7$, $R^8$, $R^{11}$ and $R^{12}$ is other than hydrogen, and when $R^1$, $R^2$, $R^3$, $R^4$, $R^5$, $R^6$, $R^7$, and $R^8$ are selected from hydrogen, halo, alkyl and alkoxy, then $R^{11}$ and $R^{12}$ are other than hydrogen and alkyl; and $R^{20}$ and $R^{21}$ are defined as for $R^1$, $R^2$, $R^3$, $R^4$, $R^5$, $R^6$, $R^7$, and $R^8$.

26. The kit of claim 23, wherein the DIM-related indole is selected from the group consisting of: diindolylmethane (DIM), hydoxylated DIMs, methoxylated DIMs, 2-(Indol-3-ylmethl)-3,3'-diindolylmethane (LTR), hydroxylated LTRs, methoxylated LTRs, 5,5'-dimethylDIM (5-Me-DIM), 2,2'-dimethylDIM (2-Me-DIM), 5,5'-dichloroDIM (5-Cl-DIM), imidazolelyl-3,3'-diindolylmethane, nitro-substituted imidazolelyl-3,3'-diindolylmethanes, 2,10-dicarbethoxy-6-methoxy-5,7-dihydro-indolo-[2,3-b]carbazole, 6-ethoxycarbonyloxy-5,7-dihydro-indolo-[2,3-b]carbazole and 2,10-dicarbethoxy-6-ethoxycarbonyloxy-5,7-dihydro-indolo-[2,3-b]carbazole, and 2,6-dicarbethoxy-3,3'-dimethyl-13,14-diindolylmethane.

27. The kit of claim 23, wherein the DIM-related indole is DIM.

28. The kit of claim 27, wherein the DIM is processed DIM.

29. The kit of claim 23, wherein the DIM-related indole is microencapsulated with phosphatidylcholine (PC), complexed with PC, or made into rapidly dissolving microparticles and nanoparticles.

30. The kit of claim 28, which comprises one or more capsules or tablets each comprising 150 to 300 mg of the processed DIM.

31. The kit of claim 23, which comprises a suspension that provides the DIM-related indole in a concentration of 15-30 mg/ml.

32. The kit of claim 23, wherein the DIM-related indole is in an amount from 50 to 500 mg.

33. A composition comprising: (i) a DIM-related indole, and (ii) an anti-protozoal agent, wherein the anti-protozoal agent is nifurtimox, benznidazole or a campothectin; and wherein the composition is formulated for oral or intravenous administration.

34. The composition of claim 33, wherein the DIM-related indole is in an amount effective to inhibit the growth of *Trypanosoma Cruzi*.

35. The composition of claim 33, wherein the DIM-related indole is selected from the group consisting of:
a compound of formula I:

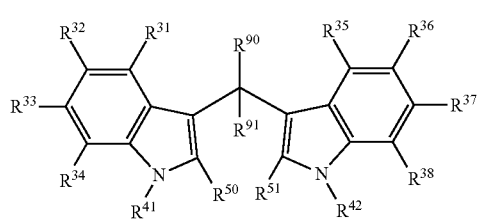

(I)

wherein $R^{32}$ and $R^{36}$ are substituents independently selected from the group consisting of hydrogen, hydroxyl, and methoxy, and ethoxycarbonyl groups, $R^{33}$ and $R^{37}$ are substituents independently selected from the group consisting of hydrogen, hydroxyl, and methoxy, $R^{31}$, $R^{34}$, $R^{35}$, $R^{38}$, $R^{41}$, and $R^{42}$ are hydrogen, $R^{50}$, $R^{51}$ are either hydrogen or methyl, and $R^{90}$, $R^{91}$ are hydrogen;

a compound of formula II:

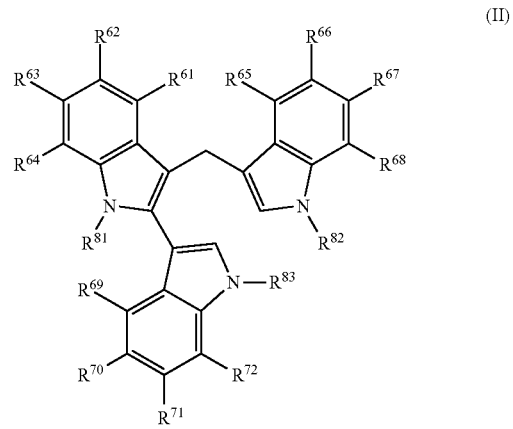

(II)

wherein $R^{62}$, $R^{63}$, $R^{66}$, $R^{67}$, $R^{70}$, and $R^{71}$ are substituents independently selected from the group consisting of hydrogen, hydroxyl, and methoxy, and $R^{61}$, $R^{64}$, $R^{65}$, $R^{68}$, $R^{69}$, $R^{72}$, $R^{81}$, $R^{82}$, and $R^{83}$ are hydrogen;

a compound of formula (IV):

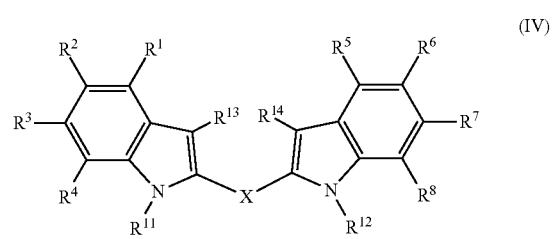

(IV)

wherein $R^1$, $R^2$, $R^3$, $R^4$, $R^5$, $R^6$, $R^7$, and $R^8$ are substituents independently selected from the group consisting of hydrogen, $C_1$-$C_{24}$ alkyl, $C_2$-$C_{24}$ alkenyl, $C_2$-$C_{24}$ alkynyl, $C_5$-$C_{20}$ aryl, $C_6$-$C_{24}$ alkaryl, $C_6$-$C_{24}$ aralkyl, halo, hydroxyl, sulfhydryl, $C_1$-$C_{24}$ alkoxy, $C_2$-$C_{24}$ alkenyloxy, $C_2$-$C_{24}$ alkylyloxy, $C_5$-$C_{20}$ aryloxy, acyl, $C_2$-$C_{24}$ alkoxycarbonyl, $C_6$-$C_{20}$ aryloxycarbonyl, halocarbonyl, $C_2$-$C_{24}$ alkylcarbonato, $C_6$-$C_{20}$ arylcarbonato, carboxy, carboxylato, carbamoyl, mono-($C_1$-$C_{24}$ alkyl)-substituted carbamoyl, di-($C_1$-$C_{24}$ alkyl)-substituted carbamoyl, mono-substituted arylcarbamoyl, thiocarbamoyl, carbamido, cyano isocyano, cyanato, isocyanato, isothiocyanato, azido, formyl, thioformyl, amino, mono- and di-($C_1$-$C_{24}$ alkyl)-substituted amino, mono- and di-(($C_5$-$C_{20}$ aryl)-substituted amino, $C_2$-$C_{24}$ allkylamido, $C_5$-$C_{20}$ arylamido, imino, alkylimino, arylimino, nitro, nitroso, sulfo, sulfonato, $C_1$-$C_{24}$ alkylsulfanyl, arylsulfanyl, $C_1$-$C_{24}$ alkylsulfinyl, $C_5$-$C_{20}$ arylsulfinyl, $C_1$-$C_{24}$ alkylsulfonyl, $C_5$-$C_{20}$ arylsulfonyl, phosphono, phosphonato, phosphinato, phospho, phosphino, and combinations thereof, and further wherein any two adjacent (ortho) substituents may be linked to form a cyclic structure selected from five-membered rings, six-membered rings, and fused five-membered and/or six-membered rings, wherein the cyclic structure is aromatic, alicyclic, heteroaromatic, or heteroalicyclic, and has zero to 4 non-hydrogen substituents and zero to 3 heteroatoms, with the proviso that one but not both of $R^2$ and $R^6$ is amino, mono-substituted amino, or di-substituted amino;

$R^{11}$ and $R^{12}$ are independently selected from the group consisting of hydrogen, $C_1$-$C_{24}$ alkyl, $C_2$-$C_{24}$ alkoxycarbonyl, amino-substituted $C_1$-$C_{24}$ alkyl, ($C_1$-$C_{24}$ alkylatnino)-substituted $C_1$-$C_{24}$ alkyl, and di-($C_1$-$C_{24}$ alkyl)amino-substituted $C_1$-$C_{24}$ alkyl, $R^{13}$ and $R^{14}$ are defined as for $R^1$, $R^2$, $R^3$, $R^4$, $R^5$, $R^6$, $R^7$, and $R^8$, with the proviso that at least one of $R^{13}$ and $R^{14}$ is other than hydrogen, and X is O, S, arylene, heteroarylene, $CR^{15}R^{16}$ or $NR^{17}$ wherein $R^{15}$ and $R^{16}$ are hydrogen, $C_1$-$C_6$ alkyl, or together form $=CR^{18}R^{19}$ where $R^{18}$ and $R^{19}$ are hydrogen or $C_1$-$C_6$ alkyl, and $R^{17}$ is as defined for $R^{11}$ and $R^{12}$; and a compound of formula (V):
hydrogen, halo, alkyl and alkoxy, then $R^{11}$ and $R^{12}$ are other than hydrogen and alkyl; and
$R^{20}$ and $R^{21}$ are defined as for $R^1$, $R^2$, $R^3$, $R^4$, $R^5$, $R^6$, $R^7$, and $R^8$.

36. The composition of claim 33, wherein the DIM-related indole is selected from the group consisting of: diindolylmethane (DIM), hydoxylated DIMs, methoxylated DIMs, 2-(Indol-3-ylmethyl)-3,3'-diindolylmethane (LTR), hydroxylated LTRs, methoxylated LTRs, 5,5'-dimethylDIM (5-Me-DIM), 2,2'-dimethylDIM (2-Me-DIM), 5,5'-dichloroDIM (5-Cl-DIM), imidazolelyl-3,3'-diindolylmethane, nitro-substituted imidazolelyl-3,3'-diindolylmethanes, 2,10-dicarbethoxy-6-methoxy-5,7-dihydro-indolo-[2,3-b]carbazole, 6-ethoxycarbonyloxy-5,7-dihydro-indolo-[2,3-b]carbazole and 2,10-dicarbethoxy-6-ethoxycarbonyloxy-5,7-dihydro-indolo-[2,3-b]carbazole, and 2,6-dicarbethoxy-3,3'-dimethyl-13,14-diindolylmethane.

37. The composition of claim 33, wherein the DIM-related indole is DIM.

38. The composition of claim 37, wherein the DIM is processed DIM.

39. The composition of claim 37, wherein the DIM is formulated for enhanced absorption, and wherein the DIM is in an amount from 25 to 750 mg.

40. The composition of claim 39, wherein the DIM is in an amount from 50 to 250 mg.

41. The composition of claim 38, wherein the processed DIM is in an amount from 150 to 300 mg.

42. A composition comprising: (i) a DIM-related indole, and (ii) an anti-protozoal agent, wherein the anti-protozoal agent is nifurtimox or benznidazole;
wherein the DIM-related indole and the anti-protozoal agent are formulated in the same composition for oral administration; and wherein the DIM-related indole is selected from the group consisting of: diindolylmethane (DIM), hydoxylated DIMs, methoxylated DIMs, 2-(Indol-3-ylmethyl)-3,3'-diindolylmethane (LTR), hydroxylated LTRs, methoxylated LTRs, 5,5'-dimethylDIM (5-Me-DIM), 2,2'-dimethylDIM (2-Me-DIM), 5,5'-dichloroDIM (5-Cl-DIM), imidazolelyl-3,3'-diindolylmethane, nitro-substituted imidazolelyl-3,3'-diindolylmethanes, 2,10-dicarbethoxy-6-methoxy-5,7-dihydro-indolo-[2,3-b]carbazole, 6-ethoxycarbonyloxy-5,7-dihydro-indolo-[2,3-b]carbazole and 2,10-dicarbethoxy-6-ethoxycarbonyloxy-5,7-dihydro-indolo-[2,3b]carbazole, and 2,6-dicarbethoxy-3,3'-dimethyl-13,14-diindolylmethane.

43. The composition of claim 42, wherein the compositio is in a form of a suspension or a pill.

44. The composition of claim 42, wherein the DIM-related indole is DIM.

45. The composition of claim 42, DIM-related indole is in an amount from 50 to 500 mg.

46. The composition of claim 44, wherein the DIM is formulated for enhanced absorption, and wherein the DIM is in an amount from 25 to 750 mg.

* * * * *